United States Patent
Herold et al.

(10) Patent No.: US 7,851,634 B2
(45) Date of Patent: Dec. 14, 2010

(54) 5-AMINO 4-HYDROXY-7-(1H-INDOLMETHYL)-8-METHYLNONAMIDE DERIVATIVES AS RENIN INHIBITORS FOR THE TREATMENT OF HYPERTENSION

(75) Inventors: Peter Herold, Basel (CH); Stefan Stutz, Basel (CH); Robert Mah, Muttenz (CH); Vincenzo Tschinke, Binningen (CH); Aleksandar Stojanovic, Basel (CH); Nathalie Jotterand, Basel (CH); Michael Quirmbach, Basel (CH); Dirk Behnke, Grenzach-Wyhlen (CH); Christiane Marti, Baden (CH)

(73) Assignee: Novartis AG, Basel (CH)

( * ) Notice: Subject to any disclaimer, the term of this patent is extended or adjusted under 35 U.S.C. 154(b) by 821 days.

(21) Appl. No.: 10/593,460

(22) PCT Filed: Mar. 17, 2005

(86) PCT No.: PCT/EP2005/051244

§ 371 (c)(1),
(2), (4) Date: Sep. 19, 2006

(87) PCT Pub. No.: WO2005/090305

PCT Pub. Date: Sep. 29, 2005

(65) Prior Publication Data

US 2008/0280895 A1 Nov. 13, 2008

(30) Foreign Application Priority Data

Mar. 19, 2004 (CH) .................................. 0469/04

(51) Int. Cl.
*C07D 405/02* (2006.01)
*A61K 31/44* (2006.01)
(52) U.S. Cl. .................................. 546/282.1; 514/336
(58) Field of Classification Search .............. 546/282.1; 514/336
See application file for complete search history.

(56) References Cited

U.S. PATENT DOCUMENTS

| | | |
|---|---|---|
| 5,559,111 A | 9/1996 | Göschke et al. |
| 5,606,078 A | 2/1997 | Göschke et al. |
| 5,627,182 A | 5/1997 | Göschke et al. |
| 5,646,143 A | 7/1997 | Göschke et al. |
| 5,654,445 A | 8/1997 | Göschke et al. |
| 5,659,065 A | 8/1997 | Göschke |
| 5,705,658 A | 1/1998 | Göschke et al. |

FOREIGN PATENT DOCUMENTS

| | | |
|---|---|---|
| EP | 0 678 500 | 10/1995 |
| EP | 0 678 503 | 10/1995 |
| EP | 0 678 514 | 10/1995 |
| EP | 0 702 004 | 3/1996 |
| EP | 0 716 077 | 6/1996 |
| WO | 03/103653 | 12/2003 |

OTHER PUBLICATIONS

CAPLUS abstract of WO 9106561.*
Goeschke et al. (CAPLUS Abstract Accession No. 1995:995373 (of patent family including EP 678503).*
Kubinyi (3D QSAR in Drug Design: Ligand-Protein Interactions and Molecular Similarity, vol. 2-3, Springer, 1998, 800 pages), table of contents and pp. 243-244.*

* cited by examiner

*Primary Examiner*—Robert Havlin
(74) *Attorney, Agent, or Firm*—Wenderoth, Lind & Ponack, L.L.P.

(57) ABSTRACT

The application relates to novel alkanamides of the general formula (I) where X is —$CH_2$— or >CH—OH; (A) $R^1$ is e.g. an optionally substituted heterocyclyl radical or an optionally substituted polycyclic, unsaturated hydrocarbon radical where X is hydroxymethylene; $R^2$ is $C_1$-$C_6$-alkyl or $C_3$-$C_6$-cydoalkyl; $R^3$ are each independently H, $C_1$-$C_6$-alkyl, $C_{1-6}$-alkoxycarbonyl or $C_1$-$C_6$-alkanoyl; $R^4$ is $C_1$-$C_6$-alkyl, $C_3$-$C_6$-cycloalkyl, $C_2$-$C_6$-alkenyl or unsubstituted or substituted aryl$C_1$-$C_6$-alkyl; $R^5$ is $C_1$-$C_6$-alkyl, $C_1$-$C_6$-hydroxyalkyl, $C_1$-$C_6$-alkoxy-$C_1$-$C_6$-alkyl, $C_1$-$C_6$-alkanoyloxy $C_1$-$C_6$-alkyl, $C_1$-$C_6$-aminoalkyl, $C_1$-$C_6$-alkylamino-$C_1$-$C_6$-alkyl, $C_1$-$C_6$-dialkylamino-$C_1$-$C_6$-alkyl, $C_1$-$C_6$-alkanoylamido-$C_1$-$C_6$-alkyl, HO(O)C—$C_1$-$C_6$-alkyl, $C_1$-$C_6$-alkyl-O—(O)C—$C_1$-$C_6$-alkyl, $H_2$N—C(O)—$C_1$-$C_6$-alkyl, $C_1$-$C_6$-alkyl-HN—C(O)—$C_1$-$C_6$-alkyl, ($C_1$,-$C_6$-alkyl)$_2$N—C(O)—$C_1$-$C_6$-alkyl, $C_2$-$C_8$-alkenyl, $C_2$-$C_8$-alkynyl, cyano-$C_1$-$C_6$-alkyl, halo-$C_1$-$C_6$-alkyl, optionally substituted aryl-$C_o$-$C_6$-alkyl, optionally substituted $C_3$-$C_8$-cycloalkyl-$C_o$-$C_6$-alkyl or optionally substituted heterocydyl-$C_o$-$C_6$-alkyl; to a process for their preparation and to the use of these compounds as medicines, especially as renin inhibitors for the treatment of hypertension.

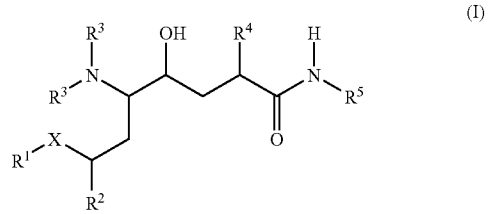

(I)

2 Claims, No Drawings

5-AMINO 4-HYDROXY-7-(1H-INDOLMETHYL)-8-METHYLNONAMIDE DERIVATIVES AS RENIN INHIBITORS FOR THE TREATMENT OF HYPERTENSION

The present invention relates to novel alkanamides, to processes for their preparation and to the use of the compounds as medicines, especially as renin inhibitors.

Alkanamides for use as medicines are known, for example, from EP 678503. However, especially with regard to renin inhibition, there is still a need for highly potent active ingredients. In this context, the improvement of the pharmacokinetic properties is at the forefront. These properties directed towards better bioavailability are, for example, absorption, metabolic stability, solubility or lipophilicity.

The invention therefore firstly provides compounds of the general formula

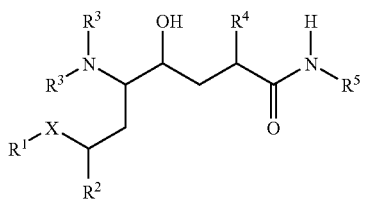

(I)

where
X is —$CH_2$— or >CH—OH;

(A) $R^1$ is an optionally substituted heterocyclyl radical or an optionally substituted polycyclic, unsaturated hydrocarbon radical where X is hydroxymethylene; or (B) $R^1$ is a heterocyclyl radical or a polycyclic, unsaturated hydrocarbon radical which is substituted by one to four radicals selected from $C_1$-$C_6$-alkyl, $C_{3-8}$-cycloalkyl, $C_{3-8}$-cycloalkoxy, $C_{3-8}$-cycloalkoxy-$C_{1-6}$-alkyl, $C_{3-8}$-cycloalkoxy-$C_{1-6}$-alkoxy, $C_1$-$C_6$-alkylamino, di-$C_1$-$C_6$-alkylamino, amino-$C_{1-6}$-alkyl, amino-$C_{2-7}$-alkoxy, polyhalo-$C_{1-6}$-alkyl, polyhalo-$C_{2-7}$-alkoxy, nitro, amino, oxo, oxide, $C_2$-$C_6$-alkenyl, $C_1$-$C_6$-alkoxy, $C_1$-$C_6$-alkanoyloxy, hydroxy, halogen, cyano, carbamoyl, carboxyl, $C_1$-$C_6$-alkylenedioxy, phenyl, phenoxy, phenylthio, phenyl-$C_1$-$C_6$-alkyl or phenyl-$C_1$-$C_6$-alkoxy, pyridylcarbonylamino-$C_{1-6}$-alkyl, $C_{2-7}$-alkenyloxy, $C_{1-6}$-alkoxy-$C_{1-6}$-alkoxy, $C_{1-6}$-alkoxy-$C_{1-6}$-alkoxy-$C_{1-6}$-alkyl, methoxybenzyloxy, hydroxybenzyloxy, methylenedioxybenzyloxy, dioxolanyl-$C_{1-6}$-alkyl, $C_{3-8}$-cycloalkyl-$C_{1-6}$-alkyl, $C_{3-8}$-cycloalkyl-$C_{1-6}$-alkoxy, hydroxy-$C_{2-7}$-alkoxy, carbamoyloxy-$C_{2-7}$-alkoxy, pyridylcarbamoyloxy-$C_{2-7}$-alkoxy, benzoyloxy-$C_{2-7}$-alkoxy, $C_{1-6}$-alkoxycarbonyl, $C_{1-6}$-alkylcarbonylamino, $C_{1-6}$-alkylcarbonylamino-$C_{1-6}$-alkyl $C_{1-6}$-alkylcarbonylamino-$C_{2-7}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$-alkylcarbonylamino-$C_{2-7}$-alkoxy, $C_{3-8}$-cycloalkyl-carbonylamino-$C_{1-6}$-alkyl, $C_{3-8}$-cycloalkylcarbonylamino-$C_{2-7}$-alkoxy, $C_{1-6}$-alkoxy-$C_{1-6}$-alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{2-6}$-alkoxy, cyano-$C_{1-6}$-alkyl, cyano-$C_{1-6}$-alkoxy, 2-oxooxazolidinyl-$C_{1-6}$-alkyl, $C_{1-6}$-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)$C_{1-6}$-alkylsulphonylamino-$C_{2-7}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxy-carbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, $C_{1-6}$-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)$C_{1-6}$-alkoxy-$C_{1-6}$-alkylcarbonylamino, 1-$C_{1-6}$-alkoxy-$C_{1-6}$-alkylimidazol-2-yl, $C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N-dimethylhydroxylamino-$C_{1-6}$-alkyl, $C_{3-6}$-cycloalkyl-$C_{1-6}$-alkanoyl, aryl-$C_{1-6}$-alkanoyl or heterocyclyl-$C_{1-6}$-alkanoyl, each of which is optionally substituted by halogen, $C_1$-$C_6$-alkyl, $C_{1-6}$-alkoxy, hydroxy $C_1$-$C_6$-alkylamino, di-$C_1$-$C_6$-alkylamino, $C_{1-6}$-alkoxycarbonyl, hydroxy-$C_{1-6}$-alkyl or trifluoromethyl, and also pyridyl, pyridyloxy, pyridylthio, pyridylamino, pyridyl-$C_{1-6}$-alkyl, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl-$C_{1-6}$-alkoxy, thienyl, thienyl-$C_{1-6}$-alkyl, thienyl-$C_{1-6}$-alkoxy, furyl, furyl-$C_{1-6}$-alkyl or furyl-$C_{1-6}$-alkoxy, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]triazol-1-ylalkyl, [1,2,4]triazol-1-ylalkoxy, [1,2,4]triazol-4-ylalkyl, [1,2,4]triazol-4-ylalkoxy, [1,2,4]oxadiazol-5-ylalkyl, [1,2,4]oxadiazol-5-yl-alkoxy, 3-methyl[1,2,4]oxadiazol-5-ylalkyl, 3-methyl[1,2,4]oxadiazol-5-ylalkoxy, 5-methyl[1,2,4]oxadiazol-3-ylalkyl, 5-methyl[1,2,4]oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy or N-methylpiperazinoalkyl, N-methylpiperazinoalkoxy, N-methylpiperazinoalkoxyalkyl, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl, 2-oxotetrahydropyrimidinyl, each of which is optionally substituted by halogen, $C_{1-6}$-alkyl, $C_{1-6}$-alkoxy or dihydroxy-$C_{1-6}$-alkylaminocarbonyl, and the —O—CH$_2$CH(OH)CH$_2$NR$_x$ radical where NR$_x$ is a mono- or di-$C_{1-6}$-alkylamino, piperidino, morpholino, piperazino or N-methylpiperazino radical, where, in the case that $R^1$ is naphthyl or cyclohexenophenyl, at least the ring system not bonded to X is substituted as specified; or (C) $R^1$ is pyrazinyl, triazolyl, imidazolyl, benzthiazolyl, pyranyl, tetrahydropyranyl, azetidinyl, morpholinyl, quinazolinyl, quinoxalinyl, isoquinolyl, benzo[b]thienyl, isobenzofuranyl, benzimidazolyl, 2-oxobenzimidazolyl, oxazolyl, thiazolyl, pyrrolyl, pyrazolyl, triazinyl, dihydrobenzofuranyl, 2-oxodihydrobenzo[d][1,3]oxazinyl, 4-oxodihydroimidazolyl, 5-oxo-4H-[1,2,4]triazinyl, 3-oxo-4H-benzo[1,4]thiazinyl, tetrahydroquinoxalinyl, 1,1,3-trioxodihydro-2H-1$\lambda^6$-benzo[1,4]thiazinyl, 1-oxopyridyl, dihydro-3H-benzo-[1,4]oxazinyl, 2-oxotetrahydrobenzo[e][1,4]diazepinyl, 2-oxodihydrobenzo[e][1,4]-diazepinyl, 1H-pyrrolizinyl, phthalazinyl, 1-oxo-3H-isobenzofuranyl, 4-oxo-3H-thieno-[2,3-d]pyrimidinyl, 3-oxo-4H-benzo[1,4]oxazinyl, [1,5]naphthyridyl, dihydro-2H-benzo-[1,4]thiazinyl, 1,1-dioxodihydro-2H-benzo[1,4]thiazinyl, 2-oxo-1H-pyrido[2,3-b][1,4]-oxazinyl, dihydro-1H-pyrido[2,3-b][1,4]oxazinyl, 1H-pyrrolo[2,3-b]pyridyl, benzo-[1,3]dioxolyl, benzooxazolyl, 2-oxobenzooxazolyl, 2-oxo-1,3-dihydroindolyl, 2,3-dihydroindolyl, indazolyl, benzofuranyl, dioxolanyl, dioxanyl, dithiolanyl, dithianyl, pyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, tetrahydropyranyl, 2-oxoimidazolidinyl, 2-oxooxazolidinyl, 2-oxopiperidinyl, 2-oxopyrrolidinyl, 2-oxo[1,3]oxazinyl, 2-oxoazepanyl, or 2-oxotetrahydropyrimidinyl;

$R^2$ is $C_{1-6}$-alkyl or $C_{3-6}$-cycloalkyl;

$R^3$ are each independently H, $C_1$-$C_6$-alkyl, $C_{1-6}$-alkoxycarbonyl or $C_1$-$C_6$-alkanoyl;

$R^4$ is $C_1$-$C_6$-alkyl, $C_3$-$C_6$-cycloalkyl, $C_2$-$C_6$-alkenyl or unsubstituted or substituted aryl-$C_1$-$C_6$-alkyl;

$R^5$ is $C_1$-$C_6$-alkyl, $C_1$-$C_6$-hydroxyalkyl, $C_1$-$C_6$-alkoxy-$C_1$-$C_6$-alkyl, $C_1$-$C_6$-alkanoyloxy-$C_1$-$C_6$-alkyl, $C_1$-$C_6$-aminoalkyl, $C_1$-$C_6$-alkylamino-$C_1$-$C_6$-alkyl, $C_{1-6}$-dialkylamino-$C_1$-$C_6$-alkyl, $C_1$-$C_6$-alkanoylamido-$C_1$-$C_6$-alkyl, HO(O)C—$C_1$-$C_6$-alkyl, $C_1$-$C_6$-alkyl-O—(O)C—$C_1$-$C_6$-alkyl, H$_2$N—C(O)—$C_1$-$C_6$-alkyl, $C_1$-$C_6$-alkyl-HN—C(O)—$C_1$-$C_6$-alkyl, ($C_1$-$C_6$-alkyl)$_2$N—C(O)—$C_1$-$C_6$-alkyl, $C_2$-$C_8$-alkenyl, $C_2$-$C_8$-alkynyl, cyano-$C_1$-$C_6$-alkyl, halo-$C_1$-$C_6$-alkyl, optionally substituted aryl-$C_0$-$C_6$-alkyl, optionally substituted $C_3$-$C_8$-cycloalkyl-$C_0$-$C_6$-alkyl or optionally substituted heterocyclyl-$C_0$-$C_6$-alkyl, or a salt thereof, in particular a pharmaceutically usable salt thereof.

As alkyl, $R^2$ and $R^4$ may be linear or branched and preferably contain from 1 to 4 carbon atoms. Examples are methyl, ethyl, n- and i-propyl, n-, i- and t-butyl, pentyl and hexyl. In a preferred embodiment, $R^2$ and $R^4$ in the compounds of the formula (I) are each isopropyl.

As alkyl, $R^5$ may be linear or branched and preferably contain from 1 to 4 carbon atoms. Examples of alkyl have been specified above. Preference is given to methyl, ethyl, n- and i-propyl, n-, i- and t-butyl.

As $C_1$-$C_6$-hydroxyalkyl, $R^5$ may be linear or branched and preferably contain from 2 to 6 carbon atoms. Some examples are 2-hydroxyeth-1-yl, 2-hydroxyprop-1-yl, 3-hydroxyprop-1-yl, 2-, 3- or 4-hydroxybut-1-yl, hydroxypentyl and hydroxyhexyl.

As $C_1$-$C_6$-alkoxy-$C_1$-$C_6$-alkyl, $R^5$ may be linear or branched. The alkoxy group preferably contains from 1 to 4 carbon atoms and the alkyl group preferably from 2 to 4 carbon atoms. Some examples are 2-methoxyeth-1-yl, 2-methoxyprop-1-yl, 3-methoxyprop-1-yl, 2-, 3- or 4-methoxybut-1-yl, 2-ethoxyeth-1-yl, 2-ethoxyprop-1-yl, 3-ethoxyprop-1-yl and 2-, 3- or 4-ethoxybut-1-yl.

As $C_1$-$C_6$-alkanoyloxy-$C_1$-$C_6$-alkyl, $R^5$ may be linear or branched. The alkanoyl group contains preferably from 1 to 4 carbon atoms and the alkyl group preferably from 2 to 4 carbon atoms. Some examples are formyloxymethyl, formyloxyethyl, acetyloxyethyl, propionyloxyethyl and butyryloxyethyl.

As $C_1$-$C_6$-aminoalkyl, $R^5$ may be linear or branched and preferably contain from 2 to 4 carbon atoms. Some examples are 2-aminoethyl, 2- or 3-aminoprop-1-yl and 2-, 3- or 4-aminobut-1-yl.

As $C_1$-$C_6$-alkylamino-$C_1$-$C_6$-alkyl and $C_1$-$C_6$-dialkylamino-$C_1$-$C_6$-alkyl, $R^5$ may be linear or branched. The alkylamino group contains preferably $C_1$-$C_4$-alkyl groups and the alkyl group preferably from 2 to 4 carbon atoms. Some examples are 2-methylaminoeth-1-yl, 2-dimethylaminoeth-1-yl, 2-ethylaminoeth-1-yl, 2-ethylaminoeth-1-yl, 3-methylaminoprop-1-yl, 3-dimethylaminoprop-1-yl, 4-methylaminobut-1-yl and 4-dimethylaminobut-1-yl.

As $C_1$-$C_6$-alkanoylamido-$C_1$-$C_6$-alkyl, $R^5$ may be linear or branched. The alkanoyl group contains preferably from 1 to 4 carbon atoms and the alkyl group preferably from 1 to 4 carbon atoms. Some examples are 2-formamidoeth-1-yl, 2-acetamidoeth-1-yl, 3-propionylamidoeth-1-yl and 4-butyrylamidoeth-1-yl.

As HO(O)C—$C_1$-$C_6$-alkyl, $R^5$ may be linear or branched, and the alkyl group preferably contains from 2 to 4 carbon atoms. Some examples are carboxymethyl, carboxyethyl, carboxypropyl and carboxybutyl.

As $C_1$-$C_6$-alkyl-O—(O)C—$C_1$-$C_6$-alkyl, $R^5$ may be linear or branched, and the alkyl groups preferably each independently contain from 1 to 4 carbon atoms. Some examples are methoxycarbonylmethyl, 2-methoxycarbonyleth-1-yl, 3-methoxycarbonylprop-1-yl, 4-methoxycarbonylbut-1-yl, ethoxycarbonylmethyl, 2-ethoxycarbonyleth-1-yl, 3-ethoxycarbonylprop-1-yl, 4-ethoxycarbonylbut-1-yl.

As H$_2$N—C(O)—$C_1$-$C_6$-alkyl, $R^5$ may be linear or branched, and the alkyl group preferably contains from 2 to 6 carbon atoms. Some examples are carbamidomethyl, 2-carbamidoeth-1-yl, 2-carbamido-2,2-dimethyleth-1-yl, 2- or 3-carbamidoprop-1-yl, 2-, 3- or 4-carbamidobut-1-yl, 3-carbamido-2-methylprop-1-yl, 3-carbamido-1,2-dimethylprop-1-yl, 3-carbamido-3-methylprop-1-yl, 3-carbamido-2,2-dimethylprop-1-yl, 2-, 3-, 4- or 5-carbamidopent-1-yl, 4-carbamido-3,3- or -2,2-dimethylbut-1-yl.

As $C_1$-$C_6$-alkyl-HN—C(O)—$C_1$-$C_6$-alkyl or ($C_1$-$C_6$-alkyl)$_2$N—C(O)—$C_1$-$C_6$-alkyl, $R^5$ may be linear or branched, and the NH-alkyl group contains preferably from 1 to 4 carbon atoms, and the alkyl group preferably from 2 to 6 carbon atoms. Examples are the aforementioned carbamidoalkyl groups whose nitrogen atom is substituted by one or two methyl, ethyl, propyl or butyl.

Halogen means, for example, F, Cl, Br or I, preferably F or Cl.

Examples of $C_1$-$C_6$-alkyl and -alkoxy radicals are methyl, ethyl, n-propyl, isopropyl, n-butyl, isobutyl, sec-butyl, tert-butyl, pentyl, hexyl, and methoxy, ethoxy, propoxy, isopropoxy, butoxy, isobutoxy, sec-butoxy and tert-butoxy respectively.

$C_1$-$C_6$-Alkylenedioxy radicals are preferably methylenedioxy, ethylenedioxy and propylenedioxy. Examples of $C_1$-$C_6$-alkanoyl radicals are acetyl, propionyl and butyryl.

Cycloalkyl means a saturated, cyclic hydrocarbon radical having 3-8 carbon atoms, for example cyclopropyl, cyclobutyl, cyclopentyl and cyclohexyl.

$C_1$-$C_6$-Alkylene radicals are, for example, methylene, ethylene, propylene, 2-methylpropylene, tetra-, penta- and hexamethylene; $C_2$-$C_6$-alkenylene radicals are, for example, vinylene and propenylene; $C_2$-$C_6$-alkynylene radicals are, for example, ethynylene; acyl radicals are alkanoyl radicals, preferably $C_1$-$C_6$-alkanoyl radicals, or aroyl radicals such as benzoyl. Aryl denotes mono- or polycyclic aromatic radicals which may be mono- or polysubstituted, for example phenyl, substituted phenyl, naphthyl, substituted naphthyl, tetrahydronaphthyl or substituted tetrahydronaphthyl.

Examples of substituents on aryl radicals, heterocyclyl radicals and polycyclic, unsaturated hydrocarbon radicals are $C_1$-$C_6$-alkyl, $C_{3-8}$-cycloalkyl, $C_{3-8}$-cycloalkoxy, $C_{3-8}$-cycloalkoxy-$C_{1-6}$-alkyl, $C_{3-8}$-cycloalkoxy-$C_{1-6}$-alkoxy, $C_1$-$C_6$-alkylamino, di-$C_1$-$C_6$-alkylamino, amino-$C_{1-6}$-alkyl, amino-$C_{2-7}$-alkoxy, polyhalo-$C_{1-6}$-alkyl, in particular trifluoromethyl, polyhalo-$C_{2-7}$-alkoxy, nitro, amino, $C_2$-$C_6$-alkenyl, $C_2$-$C_6$-alkynyl, $C_1$-$C_6$-alkoxy, $C_1$-$C_6$-alkanoyloxy, hydroxy, halogen, oxo, oxide, cyano, carbamoyl, carboxyl, $C_1$-$C_6$-alkylenedioxy, phenyl, phenoxy, phenylthio, phenyl-$C_1$-$C_6$-alkyl, phenyl-$C_1$-$C_6$-alkoxy, $C_1$-$C_6$-alkoxycarbonylphenyl, hydroxy-$C_{1-6}$-alkylphenyl, benzyloxy, pyridylcarbonylamino-$C_{1-6}$-alkyl, $C_{2-6}$-alkenyloxy, $C_{1-6}$-alkoxy-$C_{1-6}$-alkoxy, $C_{1-6}$-alkoxy-$C_{1-6}$-alkoxy-$C_{1-6}$-alkyl, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkyl, cyclopropyl-$C_{1-6}$-alkoxy, hydroxy-$C_{1-6}$-alkoxy, carbamoyloxy-$C_{1-6}$-alkoxy, pyridylcarbamoyloxy-$C_{1-6}$-alkoxy, benzoyloxy-$C_{1-6}$-alkoxy, $C_{1-6}$-alkoxycarbonyl, $C_{1-6}$-alkylcarbonylamino, $C_{1-6}$-alkylcarbonylamino-$C_{1-6}$-alkyl, $C_{1-6}$-alkylcarbonylamino-$C_{2-7}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$-alkylcarbonylamino-$C_{2-7}$-alkoxy, $C_{3-8}$-cycloalkylcarbonylamino-$C_{1-6}$-alkyl, $C_3$-$C_6$-cycloalkylcarbonylamino-$C_{2-7}$-alkoxy, $C_{1-6}$-alkoxy-$C_{1-6}$-alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N—$C_{1-6}$-alkyl)$C_{1-6}$-alkylsulphonylamino-$C_{1-6}$-alkyl, (N—$C_{1-6}$-alkyl)-$C_{1-6}$-alkylsulphonylamino-$C_{2-7}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxy-carbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, 6-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N-dimethylhydroxylamino-$C_{1-6}$-alkyl, $C_{3-6}$-cycloalkyl-$C_{1-6}$-alkanoyl, aryl-$C_{1-6}$-alkanoyl or heterocyclyl-$C_{1-6}$-alkanoyl, each of which is optionally substituted by halogen, $C_1$-$C_6$-alkyl, $C_{1-6}$-alkoxy, hydroxyl, $C_1$-$C_6$-alkylamino, di-$C_1$-$C_6$-alkylamino, $C_{1-6}$-alkoxycarbonyl, hydroxy-$C_{1-6}$-alkyl or trifluoromethyl; and pyridyl, pyridyloxy, pyridylthio, pyridylamino, pyridyl-$C_{1-6}$-alkyl, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl-$C_{1-6}$-alkoxy, thienyl, thienyl-$C_{1-6}$-alkyl, thienyl-$C_{1-6}$-alkoxy, furyl, furyl-$C_{1-6}$-alkyl or furyl-$C_{1-6}$-alkoxy, each of which is optionally substituted by halogen, $C_{1-6}$-alkyl, $C_{1-6}$-alkoxyl or dihydroxy-$C_{1-6}$-alkylaminocarbonyl.

The term polycyclic, unsaturated hydrocarbon radical denotes radicals such as naphthyl, cyclohexenophenyl, indanyl and acenaphthyl, for example.

The term heterocyclyl denotes mono- or bicyclic, saturated and unsaturated heterocyclic radicals having form 1 to 4 nitrogen and/or 1 or 2 sulphur or oxygen atoms, each of which may be mono- or polysubstituted, in particular mono-, di- or trisubstituted. In addition, the term heterocyclyl encompasses the above oxo-substituted radicals. Examples of heterocyclyl radicals are azepanyl, aziridinyl, dioxolanyl, dioxanyl, dithiolanyl, dithianyl, oxepanyl, pyrrolidinyl, piperidinyl, piperazinyl, pyridyl, thiepanyl, thienyl, pyrazinyl, triazolyl, imidazolyl, benzthiazolyl, furyl, pyranyl, tetrahydrofuranyl, tetrahydropyranyl, tetrahydrothiophenyl, tetrahydrothiopyranyl, azetidinyl, pyrimidinyl, morpholinyl, thiomorpholinyl, quinazolinyl, quinolyl, quinoxalinyl, isoquinolyl, benzo[b]thienyl, isobenzofuranyl, benzoimidazolyl, oxazolyl, thiazolyl, indolyl, pyrrolyl, pyrazolyl, triazinyl, dihydrobenzofuranyl, tetrahydroquinoxalinyl, dihydro-3H-benzo[1,4]oxazinyl, 1H-pyrrolizinyl, pthalazinyl, [1,5]naphthyridyl, dihydro-2H-benzo[1,4]thiazinyl, dihydro-1H-pyrido[2,3-b][1,4]oxazinyl, 1H-pyrrolo[2,3-b]pyridyl, benzo[1,3]dioxolyl, benzooxazolyl, 2,3-dihydroindolyl, indazolyl or benzofuranyl. Examples of substituted heterocyclyl radicals are 1-methylpiperidinyl, 1-methylpyrrolidinyl, 4-methylpiperazinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopiperidinyl, 2-oxopyrrolidinyl, 2-oxo[1,3]oxazinyl, 2-oxobenzimidazolyl, 2-oxodihydrobenzo[d][1,3]oxazinyl, 4-oxodihydroimidazolyl, 5-oxo-4H-[1,2,4]triazinyl, 3-oxo-4H-benzo[1,4]thiazinyl, 1,1,3-trioxodihydro-2H-1$\lambda^6$-benzo[1,4]thiazinyl, 1-oxopyridyl, 2-oxotetrahydrobenzo[e][1,4]diazepinyl, 2-oxodihydrobenzo[e][1,4]diazepinyl, 1-oxo-3H-isobenzofuranyl, 4-oxo-3H-thieno[2,3-d]pyrimidinyl, 3-oxo-4H-benzo[1,4]oxazinyl, 1,1-dioxodihydro-2H-benzo[1,4]thiazinyl, 2-oxo-1H-pyrido[2,3-b][1,4]oxazinyl, 2-oxobenzooxazolyl, 2-oxo-1,3-dihydroindolyl, 1-methyl-1H-indazolyl, 3-methyl-1H-indazolyl, 3-methyl-1H-indolyl, 1-methyl-1H-indolyl, methoxypyridyl, 2-oxoazepanyl or 2-oxotetrahydropyrimidinyl.

In the case of $R^1$ and $R^5$, the heterocyclyl radicals may additionally also be substituted by heterocyclylalkyl, heterocyclylalkoxy, heterocyclylalkoxyalkyl or heterocydyl, for example piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]triazol-1-ylalkyl, [1,2,4]triazol-1-ylalkoxy, [1,2,4]triazol-4-ylalkyl, [1,2,4]triazol-4-ylalkoxy, [1,2,4]oxadiazol-5-ylalkyl, [1,2,4]oxadiazol-5-ylalkoxy, 3-methyl-[1,2,4]oxadiazol-5-ylalkyl, 3-methyl[1,2,4]oxadiazol-5-ylalkoxy, 5-methyl[1,2,4]oxadiazol-3-ylalkyl, 5-methyl[1,2,4]oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy or N-methylpiperazinoalkyl, N-methylpiperazinoalkoxy, N-methylpiperazinoalkoxyalkyl, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl, 2-oxotetrahydropyrimidinyl or by the —O—CH$_2$CH(OH)CH$_2$NR$_x$ radical where NR$_x$ is a mono- or di-$C_{1-6}$-alkylamino, piperidino, morpholino, piperazino or N-methylpiperazino radical.

The term polyhydroxyalkyl denotes $C_1$-$C_7$-alkyl radicals which may be substituted by 2-6 hydroxyl groups, for example glyceryl, arabityl, sorbityl, etc.

The compounds of the formula (I) have at least four asymmetric carbon atoms and can therefore be present in the form of optically pure diastereomers, diastereomer mixtures, diastereomeric racemates, mixtures of diastereomeric racemates or as a meso compounds. The invention encompasses all of these forms. Diastereomer mixtures, diastereomeric racemates or mixtures of diastereomeric racemates may be separated by customary methods, for example by column chromatography, thin-layer chromatography, HPLC and the like.

Salts of compounds having salt-forming groups are in particular acid addition salts, salts with bases or, in the presence of a plurality of salt-forming groups, in some cases also mixed salts or internal salts.

Salts are primarily the pharmaceutically usable or nontoxic salts of compounds of the formula (I).

Such salts are formed, for example, from compounds of the formula (I) with an acidic group, for example a carboxyl or sulpho group, and are, for example, the salts thereof with suitable bases, such as nontoxic metal salts derived from metals of group Ia, Ib, IIa and IIb of the Periodic Table of the Elements, for example alkali metal, in particular lithium, sodium or potassium salts, alkaline earth metal salts, for example magnesium or calcium salts, and also zinc salts or ammonium salts, including those salts which are formed with organic amines, such as optionally hydroxy-substituted mono-, di- or trialkylamines, in particular mono-, di- or tri (lower alkyl)amines, or with quaternary ammonium bases, for example methyl-, ethyl-, diethyl or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy(lower alkyl))amines, such as N,N-dimethyl-N-(2-hydroxyethyl)amine, or N-methyl-D-glucamine, or quaternary ammonium hydroxides, such as tetrabutylammonium hydroxide. The compounds of the formula I having a basic group, for example an amino group, may form acid addition salts, for example with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic, sulpho or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the α-amino acids mentioned above, and also methanesulphonic acid, ethanesulphonic acid, 2-hydroxyethanesulphonic acid, ethane-1,2-disulphonic acid, benzenesulphonic acid, 4-methylbenzenesulphonic acid, naphthalene-2-sulphonic acid, 2- or 3-phosphoglycerate, glucose-phosphate, N-cyclohexylsulphamic acid (with formation of cyclamates) or with other acidic organic compounds such as ascorbic acid. Compounds of the formula (I) with acidic and basic groups may also form internal salts.

For the isolation and purification, pharmaceutically unsuitable salts may also find use.

Preferred inventive compounds are those of the general formula (IA)

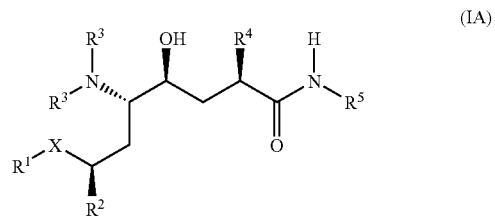

where $R^1$, $R^2$, $R^3$, $R^4$, $R^5$ and X are each as defined above for the compounds of the formula (I).

Further preferred groups of compounds of the formula (I), or more preferably of the formula (IA), are compounds in which at least one, and most preferred all, substituent(s) is (are) defined as follows:

X is $CH_2$;

$R^1$ is as as specified for (B) or (C), preferably as specified for (B);

$R^2$ is $C_1$-$C_6$-alkyl;

$R^3$ is H;

$R^4$ is $C_1$-$C_6$-alkyl;

$R^5$ is $C_1$-$C_6$-alkyl, $C_1$-$C_6$-alkoxy-$C_1$-$C_6$-alkyl, halo-$C_1$-$C_6$-alkyl, $C_2$-$C_8$-alkynyl, cyano-$C_1$-$C_6$-alkyl, optionally substituted $C_3$-$C_6$-cycloalkyl, $C_3$-$C_6$-cycloalkyl-$C_1$-$C_6$-alkyl, optionally substituted aryl, optionally substituted heterocyclyl-$C_0$-$C_6$-alkyl which, for $C_0$-alkyl, is bonded via a carbon atom or $H_2N$—C(O)—$C_1$-$C_6$-alkyl;

and pharmaceutically usable salts thereof.

Especially preferred $R^1$ radicals are benzoimidazolyl, di-$C_{1-6}$-alkoxypyrimidinyl, 2- or 5-benzo[b]thienyl, 6- or 7-isoquinolyl, 6- or 7-tetrahydroquinolyl, 6- or 7-tetrahydroisoquinolyl, 6-quinoxalinyl, 6- or 7-quinazolinyl, dihydro-3H-benzo[1,4]oxazinyl, 3,4-dihydro-2H-benzo[1,4]oxazinyl, 3-oxo-4H-benzo[1,4]oxazinyl, 2-oxobenzooxazolyl, 2-oxo-1,3-dihydroindolyl, 2,3-dihydroindolyl, indazolyl, benzofuranyl, 6 or 7-quinolyl, 6- or 7-isoquinolyl, 6- or 7-tetrahydroquinolyl, oxotetrahydroquinolyl, 6- or 7-tetrahydroisoquinolyl, 6-quinoxalinyl, 6- or 7-quinazolinyl, indolyl, 3-oxo-3,4-dihydro-2H-benzo[1,4]oxazinyl, 2-oxo-2,3-dihydrobenzooxazolyl, 2,3-dihydrobenzothiazinyl, imidazolyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl, [1,2,4]triazolo[4,3-a]pyridinyl, imidazo[1,5-a]pyridinyl, imidazo[1,2-a]pyrimidinyl, naphthyl and cyclohexenophenyl, each of which is substituted by from one to four radicals selected from hydroxy, halogen, oxo, oxide, carbamoyl, carboxyl, cyano, trifluoromethyl, $C_{1-6}$-alkyl, $C_{1-6}$-alkoxy, hydroxy-$C_{1-6}$-alkoxy, $C_{1-6}$-alkoxy-$C_{1-6}$-alkyl, $C_{1-6}$-alkoxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkoxy, pyridylcarbamoyloxy-$C_{1-6}$-alkoxy, 3-morpholino-2-hydroxypropoxy, benzyloxy-$C_{1-6}$-alkoxy, picolyloxy, $C_{1-6}$-alkoxycarbonyl, $C_{1-6}$-alkoxy-$C_{1-6}$-alkoxy-$C_{1-6}$-alkyl, $C_{1-6}$-alkylcarbonylamino, $C_{1-6}$-alkylcarbonylamino-$C_{1-6}$-alkyl, $C_{1-6}$-alkylcarbonylamino-$C_{1-6}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$-alkylcarbonylamino-$C_{1-6}$-alkoxy, $C_{3-6}$-cycloalkylcarbonylamino-$C_{1-6}$-alkyl, $C_{3-6}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{1-6}$-alkoxy-$C_{1-6}$-alkyl, hydroxy-$C_{1-6}$-alkoxy-$C_{1-6}$-alkoxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy $C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, $C_{1-6}$-alkylamino-$C_{1-6}$-alkyl, $C_{1-6}$-alkylamino-$C_{1-6}$-alkoxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, 6-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbamoyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-C alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]triazol-1-ylalkyl, [1,2,4]triazol-1-ylalkoxy, [1,2,4]triazol-4-ylalkyl, [1,2,4]triazol-4-ylalkoxy, [1,2,4]oxadiazol-5-ylalkyl, [1,2,4]oxadiazol-5-ylalkoxy, 3-methyl[1,2,4]oxadiazol-5-ylalkyl, 3-methyl[1,2,4]oxadiazol-5-ylalkoxy, 5-methyl[1,2,4]oxadiazol-3-ylalkyl, 5-methyl[1,2,4]oxadiazol-3-ylalkoxy, tetrazol-1-yl-alkyl, tetrazol-1-ylalkoxy, tetrazol-2-ylalkyl, tetrazol-2-ylalkoxy, tetrazol-5-ylalkyl, tetrazol-5-yl-alkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl and 2-oxotetrahydropyrimidinyl, where, in the case of naphthyl, or cyclohexenophenyl, at least the ring system not bonded to X is substituted as specified.

Further especially preferred $R^1$ radicals are heterocyclic radicals, in particular benzoimidazolyl, 3,4-dihydro-2H-benzo[1,4]oxazinyl, indazolyl, benzofuranyl, indolyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl, [1,2,4]triazolo[4,3-a]pyridinyl, imidazo[1,5-a]pyridinyl and imidazo[1,2-a]pyrimidinyl, each of which is substituted by from one to four radicals selected from hydroxy, halogen, oxo, oxide, carbamoyl, carboxyl, cyano, trifluoromethyl, $C_{1-6}$-alkyl, $C_{1-6}$-alkoxy, hydroxy-$C_{1-6}$-alkoxy, $C_{1-6}$-alkoxy-$C_{1-6}$-alkyl and $C_{1-6}$-alkoxy-$C_{1-6}$-alkoxy.

The compounds of the formula (I) may be prepared in an analogous manner to the preparation processes known from the literature. Similar preparation processes are described, for example, in EP 678503, WO 01/09079, WO 01/09083, WO 02/02487, WO 02/02500, WO 02/02508, WO 02/08172, WO 02/092828 and in Helvetica Chemica Acta 86 (2003), 2848-2870 and literature cited there (scheme).

in this invention also encompasses its prodrug derivative and salt form, where this is possible and appropriate.

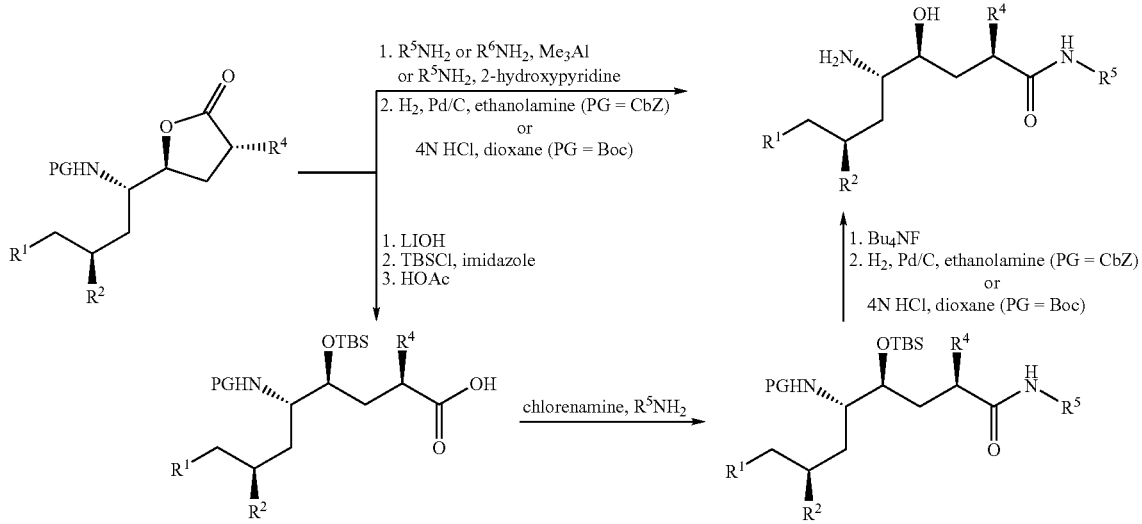

Details of the specific preparation variants can be taken from the examples.

The compounds of the formula (I) may also be prepared in optically pure form. The separation into antipodes may be effected by methods known per se, either preferably at a synthetically early stage by salt formation with an optically active acid, for example (+)- or (−)-mandelic acid and separation of the diastereomeric salts by fractional crystallization, or preferably at a rather later stage by derivatization with a chiral auxiliary building block, for example (+)- or (−)-camphanoyl chloride, and separation of the diastereomeric products by chromatography and/or crystallization and subsequent cleavage of the bond to the chiral auxiliary. To determine the absolute configuration of the piperidine present, the pure diastereomeric salts and derivatives may be analysed with common spectroscopic methods, of which X-ray spectroscopy on single crystals constitutes a particularly suitable method.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically usable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the dose relationship between a free compound, a prodrug derivative and a salt compound, a certain compound in this invention also encompasses its prodrug derivative and salt form, where this is possible and appropriate.

The compounds of the formula (I) also include those compounds in which one or more atoms are replaced by their stable, non-radioactive isotopes; for example, a hydrogen atom by deuterium.

The compounds of the formula (I) and of the formula (IA), and the pharmaceutically usable salts thereof, have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the release of the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

One experimental method of detecting the action of renin inhibitors is by means of in vitro tests, in which the reduction of the formation of angiotensin I in different systems (human plasma, purified human renin together with synthetic or natural renin substrate) is measured. One in vitro test which is used is the one according to Nussberger et. al (1987) J. Cardiovascular Pharmacol., Vol. 9, p. 39-44 which follows. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-6}$ to about $10^{-10}$ mol/l.

In salt-depleted animals, renin inhibitors bring about a blood pressure decrease. Human renin differs from renin of other species. To test inhibitors of human renin, primates (marmosets, Callithrixjacchus) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[(2-furanylmethyl)amino]benzoic acid) (5 mg/kg). 16 hours after the injection of furosemide, the test substances are administered either directly into the femoral artery by means of an injection cannula or into the stomach by gavage as a suspension or solution, and their effect on blood pressure and heart rate is evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the formula (I) and preferably of the formula (IA), and the pharmaceutically usable salts thereof, may find use as medicines, for example in the form of pharmaceutical preparations. The pharmaceutical preparations may be administered enterally, such as orally, for example in the form of tablets, coated tablets, sugar-coated tablets, hard and soft gelatine capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatine capsules, the compounds of the formula (I) and preferably of the formula (IA) and pharmaceutically usable salts thereof may be processed with pharmaceutically inert, inorganic or organic excipients. Such excipients used, for example for tablets, coated tablets and hard gelatine capsules, may be lactose, corn starch or derivatives thereof, talc, stearic acid or salts thereof etc.

Suitable excipients for soft gelatine capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formula (I) and preferably of the formula (IA), and the pharmaceutically usable salts thereof, in the treatment or prevention of hypertension and heart failure, and also glaucoma, cardiac infarction, kidney failure and restenoses.

The compounds of the formula (I) and preferably of the formula (IA), and the pharmaceutically usable salts thereof may also be administered in combination with one or more agents having cardiovascular action, for example α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyldopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formulae (I) or (IA) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The examples which follow illustrate the present invention. All temperatures are reported in degrees Celsius, pressures in mbar. Unless stated otherwise, the reactions take place at room temperature. The abbreviation "Rf=xx (A)" means, for example, that the Rf value xx is obtained in the solvent system A. The ratio of the solvents relative to one another is always reported in parts by volume. Chemical names of end products and intermediates were obtained with the aid of the program AutoNom 2000 (Automatic Nomenclature). Unless stated otherwise, the absolute stereochemistry of the "main chain substituents" is (2S,4S,5S,7S) (see formula II).

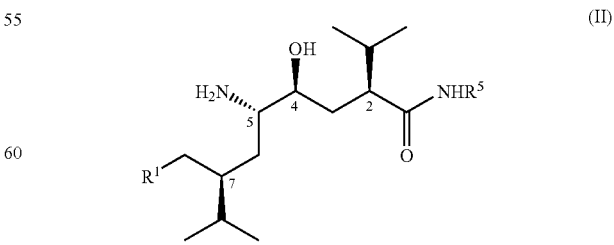

HPLC gradients on Hypersil BDS C-18 (5 μm); column: 4×125 mm

I 90% water*/10% acetonitrile* to 0% water*/100% acetonitrile* in 5 minutes+2.5 minutes (1.5 ml/min)
II 95% water*/5% acetonitrile* to 0% water*/100% acetonitrile* in 40 minutes (0.8 ml/min)
* contains 0.1% trifluoroacetic acid
The following abbreviations are used:
Rf ratio of distance traveled by a substance to separation of the eluent front from the start point in thin-layer chromatography
Rt retention time of a substance in HPLC (in minutes)
m.p. melting point (temperature)

General Method A: (N-CbZ Deprotection)
A solution of 1 mmol of "N-CbZ derivative" in 30 ml of ethanol is hydrogenated in the presence of 0.1 mmol of ethanolamine and 0.150 g of 10% Pd/C at 0-10° C. over 1-3 hours. The reaction mixture is clarified by filtration and the filtrate is concentrated by evaporation. The residue is admixed with 30 ml of 1M sodium hydrogencarbonate solution and extracted with tert-butyl methyl ether (2×). The combined organic phases are dried over sodium sulphate and filtered, and the filtrate is concentrated by evaporation. The title compound is obtained from the residue by means of flash chromatography (SiO2 60 F).

General Method B: (Lactone Amidation I)
A mixture of 1 mmol of "lactone", "amine" (5-30 equiv.) (methylamine/ethylamine are used as a 10% solution in triethylamine) and 2-hydroxypyridine (1.0 equiv.) is stirred at 40-50° C. over 2-16 hours. The reaction mixture is admixed with 30 ml of 1M sodium hydrogencarbonate solution and extracted with tert-butyl methyl ether (2×). The combined organic phases are dried over sodium sulphate and filtered, and the filtrate is concentrated by evaporation. The title compound is obtained from the residue by means of flash chromatography (SiO2 60 F).

General Method C: (Lactone Amidation II)
A solution of 1.1 mmol of trimethylaluminium solution (2M in heptane) at −78° C. is admixed with a solution of 1.2 mmol of "amine" in 1-2 ml of toluene. The reaction mixture is warmed to room temperature, stirred further for 30-60 minutes and subsequently concentrated by evaporation. The residue is admixed with a solution of 1 mmol of "lactone" in 2 ml of toluene and stirred at 80° C. over 2-4 hours. The reaction mixture is cooled to room temperature, admixed with 10 ml of 1N HCl and then stirred for a further 30 minutes. The reaction mixture is diluted with brine and extracted with toluene (2×)—the combined organic phases are dried over sodium sulphate and concentrated by evaporation. The title compound is obtained from the residue by means of flash chromatography (SiO₂ 60 F).

Residues R¹:

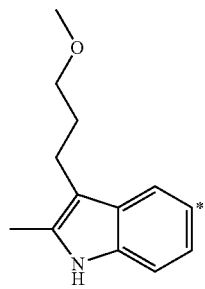
1

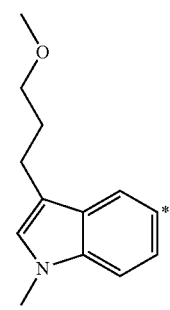
2

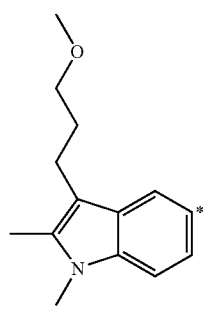
3

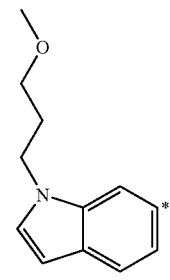
4

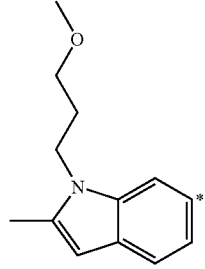
5

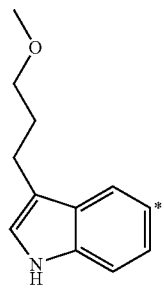
6

-continued
7
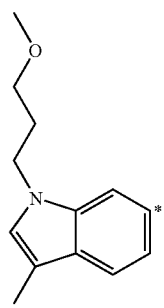
8
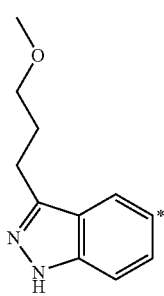
9
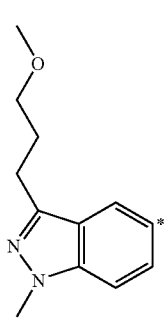
10
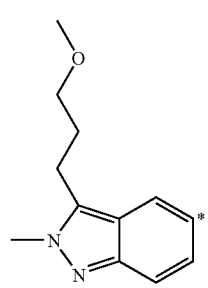
11
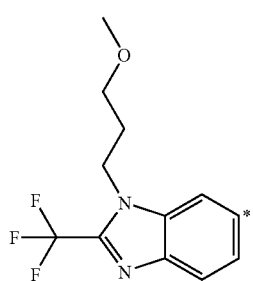
-continued
12
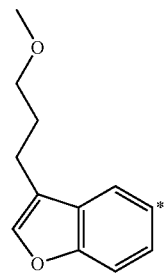
13
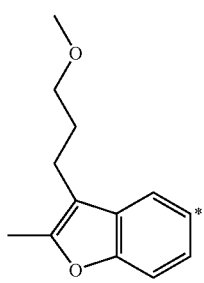
14
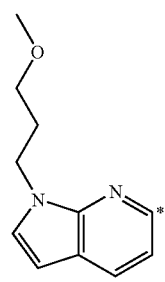
15
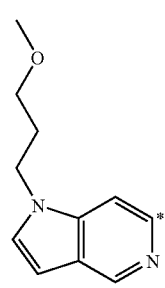
16
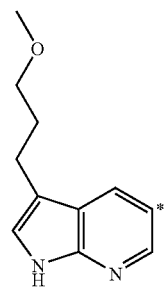

-continued

-continued
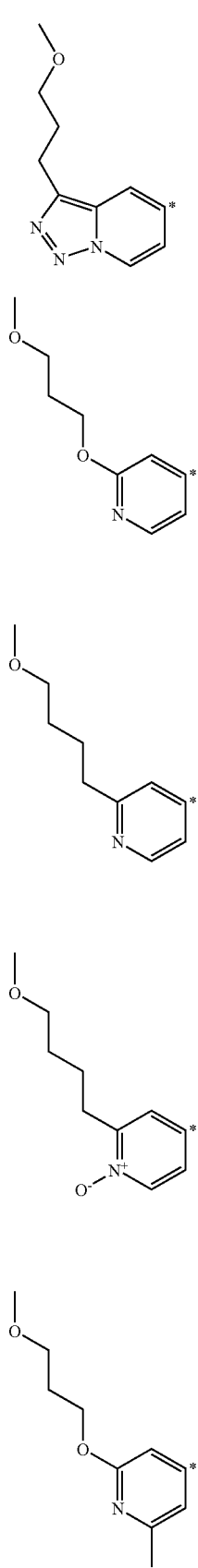
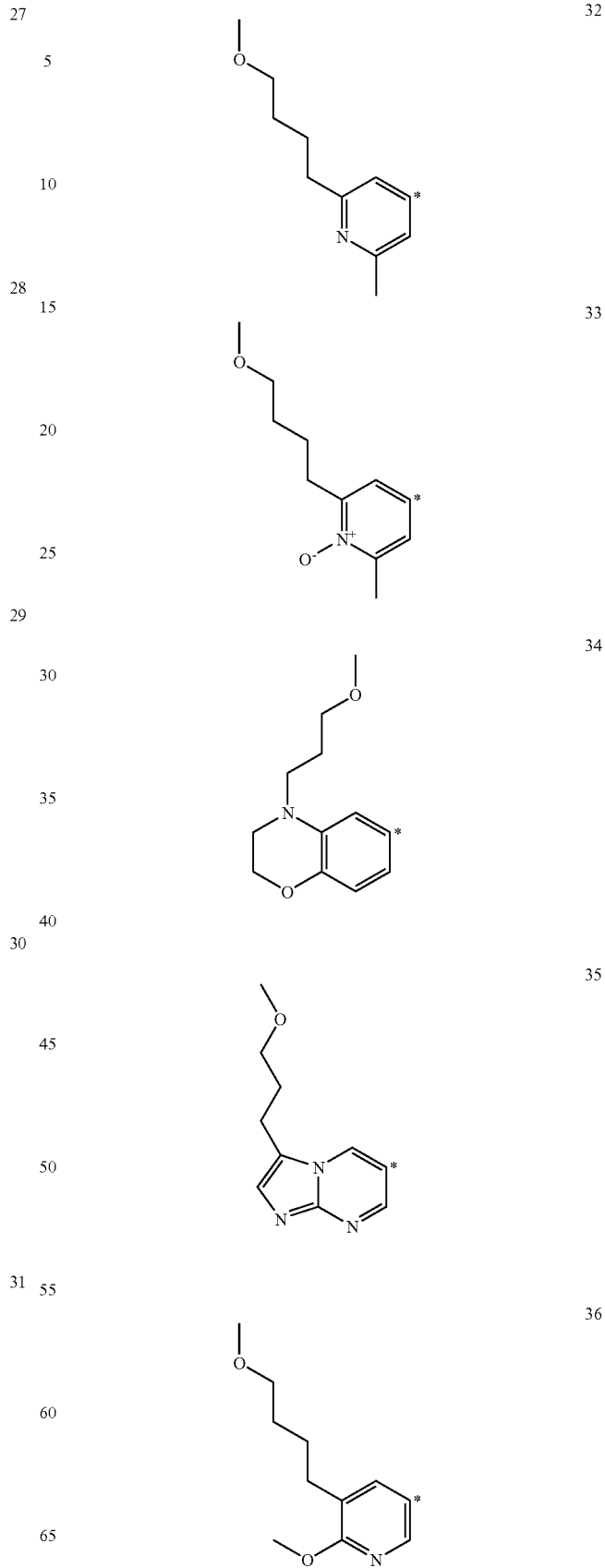

-continued

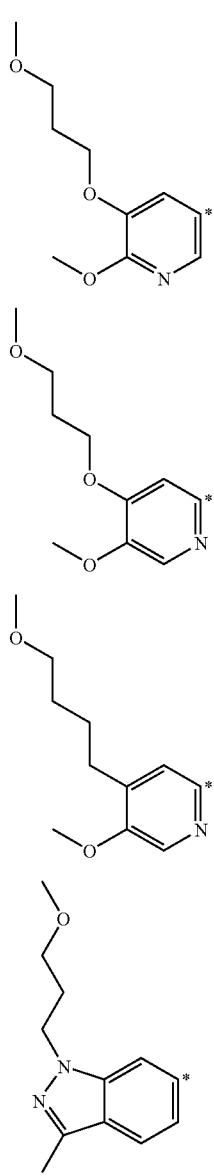

37

38

39

40

The optionally protected residues R¹ (bromide or iodide derivatives) are prepared as follows:

1 5-Bromo-3-(3-methoxypropyl)-1-(2-trimethylsilanylethoxymethyl)-1H-indole

The stirred solution of 1.0 g of 5-bromo-3-(3-methoxyprop-(E,Z)-enyl)-1-(2-trimethylsilanylethoxymethyl)-1H-indole in 40 ml of ethyl acetate is admixed at 0° C. with 0.152 ml of acetic acid and 0.402 g of 10% Pd/C. The mixture is hydrogenated at 0° C. over 1 hour, then clarified by filtration, and the filtrate is washed successively with 1M sodium hydrogencarbonate solution (cold) and brine. The organic phase is dried over sodium sulphate and filtered, and the filtrate is concentrated by evaporation. The title compound is obtained as a yellowish oil from the residue by means of flash chromatography (SiO2 60 F). Rf=0.25 (1:4 EtOAc-heptane). Rt=6.26 (gradient I).

The starting materials are prepared as follows:

a) 5-Bromo-3-(3-methoxyprop-(E,Z)-enyl)-1-(2-trimethylsilanylethoxymethyl)-1H-indole 95.3 ml of a sodium bis(trimethylsilyl)amide solution (1M in tetrahydrofuran) are added dropwise at 0° C. over 10 minutes to the stirred mixture of 37.9 g of (2-methoxyethyl)triphenylphosphonium bromide [55894-16-1] in tetrahydrofuran. The mixture is stirred at 0° C. over a further 30 minutes and a solution of 22.2 g of 5-bromo-1-(2-trimethylsilanylethoxymethyl)-1H-indole-3-carbaldehyde in 100 ml of tetrahydrofuran is subsequently added dropwise. The reaction mixture is stirred at 0° C. over a further 1 hour, quenched with 1M ammonium chloride solution, diluted with water and extracted with tert-butyl methyl ether (2×). The combined organic phases are washed with water and brine, dried over sodium sulphate and filtered, and the filtrate is concentrated by evaporation. The title compound (E,Z mixture) is obtained as a brown oil from the residue by means of flash chromatography (SiO2 60 F). Rf=0.46 (1:2 EtOAc-heptane). Rt=6.20 (gradient I).

b) 5-Bromo-1-(2-trimethylsilanylethoxymethyl)-1H-indole-3-carbaldehyde

The stirred solution of 25 g of 5-bromo-1H-indole-3-carbaldehyde [877-03-2] in 250 ml of N,N-dimethylformamide is admixed at 0° C. with 4.59 g of sodium hydride (60% in mineral oil) in portions. The mixture is stirred over 1 hour and then admixed dropwise with 22.5 ml of 2-(trimethylsilyl)ethoxymethyl chloride (SEM-Cl). The mixture is stirred at room temperature over 16 hours. The resulting reaction mixture is poured onto 350 ml of 1M sodium hydrogencarbonate solution (cold) and extracted with tert-butyl methyl ether (2×). The combined organic phases are washed successively with water (3×) and brine, dried over sodium sulphate and filtered, and the filtrate is concentrated by evaporation. The title compound is obtained as a white solid from the residue by means of crystallization (from diisopropyl ether). Rf=0.23 (1:2 EtOAc-heptane). Rt=5.58. (gradient I). m.p. 105-106° C.

5 6-Bromo-1-(3-methoxypropyl)-1H-indole

The stirred solution of 25 g of 6-bromo-1H-indole [52415-29-9] in 250 ml of DMPU is admixed at 0° C. with 11.2 g of sodium hydride (60% in mineral oil) in portions. The mixture is stirred over 1 hour and then admixed with 60.9 g of 1-chloro-3-methoxypropane and 4.71 g of tetrabutylammonium iodide (exothermic reaction). The mixture is stirred at room temperature over a further 1 hour. The resulting reaction mixture is poured onto 2 l of water (cold) and extracted with tert-butyl methyl ether (2×). The combined organic phases are washed successively with water (3×) and brine, dried over sodium sulphate and filtered, and the filtrate is concentrated by evaporation. The title compound is obtained as a slightly yellowish oil from the residue by means of flash chromatography (SiO2 60 F). Rf=0.31 (1:2 EtOAc-heptane). Rt=5.10 (gradient I).

9
5-Bromo-3-(3-methoxypropyl)-1-methyl-1H-indazole

A solution of 54.00 g of 5-bromo-3-(3-methoxyprop-1-ynyl)-1-methyl-1H-indazole in 1700 ml of methanol is admixed at room temperature with 20.58 g of 10% Pd/C. The mixture is hydrogenated over 1.5 hours and clarified by filtration, and the filtrate is concentrated by evaporation. The title compound is obtained as a yellowish oil from the residue by means of flash chromatography (SiO2 60 F). Rf=0.56 (1:1 EtOAc-heptane). Rt=4.37 (gradient I).

The starting materials are prepared as follows:

a) 5-Bromo-3-(3-methoxyprop-1-ynyl)-1-methyl-1H-indazole

A solution of 81.67 g of 5-bromo-3-iodo-1-methyl-1H-indazole in 750 ml of N,N-dimethylformamide and 335 ml of triethylamine is admixed at room temperature under argon with 25 ml of 3-methoxypropyne, 5.5 g of copper(I) iodide and 10 g of bis(triphenylphosphine)-palladium(II) chloride, and subsequently heated to 60° C. After 1 hour, the reaction mixture is cooled to room temperature, diluted with water and extracted with ethyl acetate (4x). The combined organic phases are dried over sodium sulphate and concentrated by evaporation. The title compound is obtained as a yellow solid from the residue by means of flash chromatography (SiO2 60 F). Rf=0.67 (2:1 EtOAc-heptane). Rt=4.42 (gradient I).

b) 5-Bromo-3-iodo-1-methyl-1H-indazole

A solution of 184.30 g of 5-bromo-3-iodo-1H-indazole [459133-66-5] in 2500 ml of methanol is admixed at 40° C. with 212 ml of a sodium methoxide solution (5.4M in methanol). 90 ml of methyl iodide are then added and the reaction mixture is heated to 65° C. After 30 minutes, the reaction mixture is cooled to room temperature, concentrated by evaporation to approx. 1000 ml, diluted with water and extracted with ethyl acetate (2x). The combined organic phases are dried over sodium sulphate and concentrated by evaporation. The title compound is obtained as a dark brown solid from the residue by means of flash chromatography (SiO2 60 F). Rf=0.68 (dichloromethane). Rt=4.94 (gradient I). As a by-product, the 5-bromo-3-iodo-2-methyl-2H-indazole regioisomer is also isolated as a red-orange solid. Rf=0.52 (dichloromethane). Rt=4.58 (gradient I).

11 6-Bromo-1-(3-methoxypropyl)-2-trifluoromethyl-1H-benzoimidazole 0.2 ml of concentrated, aqueous hydrochloric acid is added under an argon atmosphere to a solution of 12.83 g of 4-bromo-$N^2$-(3-methoxypropyl)benzene-1,2-diamine in 5.78 ml of trifluoroacetic acid. The reaction mixture is heated to reflux for 4 hours. 2 ml of trifluoroacetic acid are added once more and the reaction mixture is heated to reflux for a further 2 hours. The reaction mixture is cooled to room temperature and neutralized with saturated, aqueous sodium hydrogencarbonate solution. The mixture is extracted with ethyl acetate (3x). The combined organic phases are dried with sodium sulphate and concentrated by evaporation. The title compound is obtained as a yellow oil from the residue by means of flash chromatography (SiO2 60 F). Rf=0.60 (1:2 EtOAc-heptane). Rt=4.79 (gradient I).

The starting materials are prepared as follows:

a) 4-Bromo-$N^2$-(3-methoxypropyl)benzene-1,2-diamine 78.57 g of tin(II) chloride are added to a solution of 21.01 g of (5-bromo-2-nitrophenyl)-(3-methoxypropyl)amine in 950 ml of ethanol. The reaction mixture is heated to reflux for 12 hours. The mixture is cooled to room temperature and concentrated by evaporation. The residue is treated with 2M NaOH until a pH of 11 has been attained. The mixture is extracted with tert-butyl methyl ether (3x). The combined organic phases are dried with sodium sulphate and concentrated by evaporation. The title compound is obtained as an orange oil from the residue. Rf=0.31 (1:1 EtOAc-heptane). Rt=3.06 (gradient I).

b) (5-Bromo-2-nitrophenyl)-(3-methoxypropyl)amine

A solution of 26.49 g of 2,4-dibromo-1-nitrobenzene [51686-78-3] and 70 ml of 3-methoxypropylamine is stirred at room temperature for 4 hours and subsequently left to stand at 3° C. for 2 days. The reaction mixture is concentrated by evaporation. The title compound is obtained as a yellow oil from the residue by means of flash chromatography (SiO2 60 F). Rf=0.4 (1:3 EtOAc-heptane). Rt=4.99 (gradient I).

12 5-Bromo-3-(3-methoxypropyl)benzofuran

Analogously to residue 1, 6.01 g of 5-bromo-3-(3-methoxyprop-1-ynyl)benzofuran are converted. The title compound is obtained as a yellowish oil. Rf=0.55 (1:6 EtOAc-heptane); Rt=5.22 (gradient I).

The starting material is prepared as follows:

a) 5-Bromo-3-(3-methoxyprop-1-ynyl)benzofuran

Analogously to residue 9a, 9.31 g of 5-bromobenzofuran-3-yl trifluoromethanesulphonate [440083-74-9] and 3.52 ml of 3-methoxypropyne are reacted. The title compound is obtained as a yellowish oil. Rf=0.43 (1:10 EtOAc-heptane); Rt=5.14 (gradient I).

According to the process described for residues 1, 5, 9, 11 and 12, the following residues are prepared in an analogous manner:

2 5-Bromo-3-(3-methoxypropyl)-2-methyl-1H-indole
3 5-Bromo-3-(3-methoxypropyl)-1-methyl-1H-indole
4 5-Bromo-3-(3-methoxypropyl)-1,2-dimethyl-1H-indole
6 6-Bromo-1-(3-methoxypropyl)-2-methyl-1H-indole
7 6-Bromo-1-(3-methoxypropyl)-3-methyl-1H-indole
8 5-Bromo-3-(3-methoxypropyl)-1H-indazole
10 5-Bromo-3-(3-methoxypropyl)-2-methyl-2H-indazole
13 5-Bromo-3-(3-methoxypropyl)-2-methylbenzofuran
14 6-Bromo-1-(3-methoxypropyl)-1H-pyrrolo[2,3-b]pyridine
15 6-Bromo-1-(3-methoxypropyl)-1H-pyrrolo[3,2-b]pyridine
16 5-Bromo-3-(3-methoxypropyl)-1H-pyrrolo[2,3-b]pyridine
17 5-Bromo-3-(3-methoxypropyl)-1-methyl-1H-pyrrolo[2,3-b]pyridine
18 5-Bromo-3-(3-methoxypropyl)-1H-pyrrolo[2,3-c]pyridine
19 5-Bromo-3-(3-methoxypropyl)-1-methyl-1H-pyrrolo[2,3-c]pyridine
20 5-Bromo-3-(3-methoxypropyl)-1H-pyrrolo[3,2-b]pyridine
21 5-Bromo-3-(3-methoxypropyl)-1-methyl-1H-pyrrolo[3,2-b]pyridine 22 6-Bromo-3-(3-methoxypropyl)imidazo[1,5-a]pyridine A solution of 5.74 g of N-(5-bromopyridin-2-ylmethyl)-4-methoxybutyramide in 20 ml of benzene is admixed with 3.37 g of phosphorus oxychloride. The reaction mixture is heated to reflux over 5 hours. The reaction mixture is subsequently cooled to room temperature and concentrated by evaporation, and the residue is admixed with 100 ml of water. The aqueous solution is basified with saturated aqueous sodium hydrogencarbonate solution and extracted with dichloromethane (3×200 ml). The combined organic phases are washed with 200 ml of water, dried over sodium sulphate and concentrated by evaporation. The title compound is identified on the basis of the Rf value by means of flash chromatography (SiO2 60 F).

The starting material is prepared as follows:

a) N-(5-Bromopyridin-2-ylmethyl)-4-methoxybutyramide

A solution of 9.35 g of C-(5-bromopyridin-2-yl)methylamine [17399-23-0] in 200 ml of ethyl acetate is admixed with 300 ml of saturated aqueous sodium carbonate solution. The reaction mixture is cooled to 0° C. in an ice bath and subsequently admixed dropwise with a solution of 4-methoxybutanoyl chloride [61882-39-1] in 100 ml of ethyl acetate. The reaction mixture is stirred at 0° C. over 1 hour. The phases are separated and the aqueous phase is extracted with 300 ml of ethyl acetate (2×). The combined organic phases are washed with 300 ml of brine, dried over sodium sulphate and concentrated by evaporation. The title compound is identified on the basis of the Rf value from the residue by means of flash chromatography (SiO2 60 F).

23 6-Bromo-3-(3-methoxypropyl)-1-methylimidazo[1,5-a]pyridine

A solution of 1.42 g of 1,1,1-triphenyl-3-(5-bromopyridin-2-yl)-2-aza-1,$\lambda^5$-phosphabuta-1,3-diene in 10 ml of anhydrous chloroform is admixed with a solution of 0.306 g of 4-methoxybutyraldehyde [21071-24-9] in 5 ml of chloroform. The reaction solution is left to stand at room temperature over 48 hours and subsequently concentrated by evaporation. The title compound is identified on the basis of the Rf value from the residue by means of flash chromatography (SiO2 60 F).

The starting material is prepared as follows:

a) 1,1,1-Triphenyl-3-(5-bromopyridin-2-yl)-2-aza-1,$\lambda^5$-phosphabuta-1,3-diene 4.18 g of methyltriphenylphosphonium iodide are taken up under argon in 5 ml of anhydrous benzene and 6.3 ml of a methyllithium solution (1.6M in diethyl ether) are added dropwise. The solution is heated to reflux and the resulting suspension is subsequently cooled to 0° C. A solution of 1.83 g of 5-bromopyridine-2 carbonitrile [97483-77-7] in 4 ml of benzene is added and the reaction mixture is stirred at room temperature over 120 hours. Dichloromethane is added and the lithium salts are filtered off through Hyflo. The filtrate is concentrated. The title compound is identified on the basis of the Rf value from the residue by means of flash chromatography (Alox).

24 7-Bromo-1-(3-methoxypropyl)imidazo[1,5-a]pyridine

A mixture of 5.34 g of 7-bromo-1-(3-methoxypropenyl)imidazo[1,5-a]pyridine and 0.200 g of 10% Pd/C is hydrogenated at 0° C. and standard pressure in 100 ml of 1:1 ethanol/dioxane. As soon as the double bond has been reduced fully, the catalyst is filtered off through Hyflo and the filtercake is washed with methanol (2×20 ml) and the filtrate is concentrated by evaporation. The title compound is identified on the basis of the Rf value from the residue by means of flash chromatography (SiO2 60 F).

The starting materials are prepared as follows:

a) 7-Bromo-1-(3-methoxypropenyl)imidazo[1,5-a]pyridine

A suspension of 12.04 g of (2-methoxyethyl)triphenylphosphonium bromide [55894-16-1] in 50 ml of anhydrous N,N-dimethylformamide is admixed with 2.60 g of sodium hydride (60% dispersion). The reaction mixture is stirred at room temperature for 30 minutes and a solution of 6.75 g of 7-bromoimidazo[1,5-a]pyridine-1-carbaldehyde in 20 ml of N,N-dimethylformamide is added. The reaction mixture is subsequently stirred at 50° C. for 1 hour. The reaction mixture is cooled to room temperature and poured onto ice-water. The quenched mixture is acidified with 1M HCl and extracted with tert-butyl methyl ether (3×100 ml). The combined organic phases are washed with water (100 ml) and brine (100 ml), dried over sodium sulphate and concentrated by evaporation. The title compound is identified on the basis of the Rf value from the residue by means of flash chromatography (SiO2 60 F).

b) 7-Bromoimidazo[1,5-a]pyridine-1-carbaldehyde

A solution of 4.93 g of 7-bromoimidazo[1,5-a]pyridine in 2.2 ml of dry N,N-dimethylformamide is cooled to 0-5° C. in an ice bath. Phosphorus oxychloride (5.37 g) is added dropwise at 0-5° C. and the reaction mixture is subsequently stirred at 100° C. over 1 hour. The reaction mixture is cooled and poured onto ice-water. The quenched solution is basified with 25% ammonium hydroxide solution and extracted with dichloromethane (3×200 ml). The combined organic phases are dried over sodium sulphate and concentrated by evaporation. The title compound is identified on the basis of the Rf value from the residue by means of flash chromatography (SiO2 60 F).

c) 7-Bromoimidazo[1,5-a]pyridine

A solution of 10.75 g of N-(4-bromopyridin-2-ylmethyl)formamide in 100 ml of benzene is admixed with 8.43 g of phosphorus oxychloride. The reaction mixture is heated to reflux over 4 hours. The reaction mixture is subsequently cooled to room temperature and concentrated by evaporation, and the residue is admixed with 200 ml of water. The aqueous solution is basified with 1M NaOH and extracted with dichloromethane (3×300 ml). The combined organic phases are washed with 300 ml of water, dried over sodium sulphate and concentrated by evaporation. The title compound is identified on the basis of the Rf value from the residue by means of flash chromatography (SiO2 60 F).

d) N-(4-Bromopyridin-2-ylmethyl)formamide 20.00 g of C-(4-bromopyridin-2-yl)methylamine are taken up in 60 ml of formic acid and the solution is heated to reflux over 3 hours. The reaction solution is cooled to room temperature and concentrated by evaporation, and the residue is taken up in saturated aqueous sodium hydrogencarbonate solution (300 ml) and the aqueous solution extracted with dichloromethane (3×300 ml). The combined organic phases are washed with water (300 ml), dried over sodium sulphate and concentrated by evaporation. The title compound is identified on the basis of the Rf value from the residue by means of flash chromatography (SiO2 60 F).

e) C-(4-Bromopyridin-2-yl)methylamine

A solution of 18.70 g 4-bromopyridine-2-carbonitrile [62150-45-2] in 200 ml of tetrahydrofuran is admixed under argon dropwise with 500 ml of 1M borane-tetrahydrofuran complex solution. The reaction solution is subsequently left to stand at room temperature for 16 hours. The reaction solution is cooled to 0° C., admixed dropwise with 500 ml of 2M HCl and heated to reflux for 30 minutes. The reaction solution is cooled to room temperature, basified with 2M NaOH, saturated with sodium chloride and extracted with tetrahydrofuran (3×300 ml). The combined organic phases are dried over sodium sulphate and concentrated by evaporation. The title compound is identified on the basis of the Rf value from the residue by means of flash chromatography (SiO2 60 F).

25 7-Bromo-1-(3-methoxypropyl)-3-methylimidazo[1,5-a]pyridine

Analogously to residue 24, 1.0 g of 7-bromo-1-(3-methoxypropenyl)-3-methylimidazo[1,5-a]pyridine is reacted. The title compound is identified on the basis of the Rf value.

The starting materials are prepared as follows:

a) 7-Bromo-1-(3-methoxypropenyl)-3-methylimidazo[1,5-a]pyridine

A solution of 1.59 g 7-methoxy-1,1,1-triphenyl-3-(4-bromopyridin-2-yl)-2-aza-1,$\lambda^5$-phosphaheptene-1,3-diene in 10 ml of anhydrous chloroform is admixed with a solution of 0.132 g of acetaldehyde in 5 ml of chloroform. The reaction solution is left to stand at room temperature over 48 hours and subsequently concentrated by evaporation. The title compound is identified on the basis of the Rf value from the residue by means of flash chromatography (SiO2 60 F).

b) 7-Methoxy-1,1,1-triphenyl-3-(4-bromopyridin-2-yl)-2-aza-1,$\lambda^5$-phosphaheptane-1,3-diene 4.62 g of (4-methoxybutyl)triphenylphosphonium iodide are taken up under argon in 5 ml of anhydrous benzene and 6.3 ml of a methyllithium solution (1.6M in diethyl ether) are added dropwise. The solution is heated to reflux and the resulting suspension is subsequently cooled to 0° C. A solution of 1.83 g of 4-bromopyridine-2-carbonitrile [62150-45-2] in 4 ml of benzene is added and the reaction mixture is stirred at room temperature over 120 hours. Dichloromethane is added and the lithium salts are filtered off through Hyflo. The filtrate is concentrated. The title compound is identified on the basis of the Rf value from the residue by means of flash chromatography (Alox).

c) (4-Methoxybutyl)triphenylphosphonium iodide 10.70 g of 4-methoxybutyl iodide are taken up in 80 ml of acetonitrile, 14.43 g of triphenylphosphine are added and the reaction solution is heated to reflux for 16 hours. The reaction solution is concentrated by evaporation and the residue is admixed with diethyl ether. The suspension is stirred at room temperature for 30 minutes and the precipitated solid is filtered off and dried. The title compound is used without further purification for the next stage.

26 6-Bromo-3-(3-methoxypropyl)[1,2,4]triazolo[4,3a]pyridine

A mixture of 18.80 g of (5-bromopyridin-2-yl)hydrazine [CAS 77992-44-0] and 14.54 g of methyl 4-methoxybutyrate [CAS 29006-01-7] is heated to reflux over 16 hours. The reaction mixture is subsequently cooled and purified by means of flash chromatography (SiO2 60 F). The title compound is identified on the basis of the Rf value.

27 5-Bromo-3-(3-methoxy-propyl)-[1,2,3]triazolo[1,5a]pyridine

A solution of 20 mmol [1-(4-bromo-pyridin-2-yl)-4-methoxy-butylidene]-p-toluenesulfonyl hydrazone in 36 ml of morpholine ist heated at 100° C. for 3 hours. The excess morpholine is removed in vacuo und and the residue is treated with diethyl ether. The mixture is filtered and the filtrate concentrated. The residue is purified via flash chromatography (SiO2 60 F) and the title compound identified on the basis of the Rf value. The starting materials are prepared as follows:

a) [1-(4-Bromo-pyridin-2-yl)-4-methoxy-butylidene]-p-toluenesulfonyl hydrazone p-Toluenesulfonyl hydrazide (10 mmol) is added to a solution of 10 mmol of 1-(4-bromopyridin-2-yl)-4-methoxy-butan-1-one in 20 ml of methanol. The reaction solution is left to stand at room temperature for 2 hours. The solvent is removed under reduced pressure and the crude product used without further purification. The title compound is identified on the basis of the Rf value.

b) 1-(4-Bromo-pyridin-2-yl)-4-methoxy-butan-1-one

The Grignard reagent prepared from 20 mmol of 3-methoxypropylbromide and 22 mmol of magnesium in dry ether (100 ml) is added slowly to 30 mmol of 4-bromo-2-cyanopyridine in 80 ml of dry ether under argon. The reactions mixture is stirred for 12 hours at room temperature and 5M HCl is added. The mixture is made alkaline with 25% aqueous ammonium hydroxide solution and the layers are separated. The organic layer is dried over sodium sulphate and evaporated. Flash chromatography (SiO2 60 F) of the residue provides the title compound which is identified on the basis of the Rf value.

28 4-Bromo-2-(3-methoxypropoxy)pyridine 11 mmol of silver carbonate and 20 mmol of 1-iodo-3-methoxypropane [61542-10-7] are added under an argon atmosphere to a solution of 21 mmol of 4-bromo-1H-pyridin-2-one [36953-37-4] in 30 ml of benzene. The reaction mixture is heated to 45° C. with exclusion of light for 2 days. The mixture is cooled to room temperature and filtered through Hyflo. The filtercake is washed with benzene and with saturated, aqueous sodium hydrogencarbonate solution. The phases of the filtrate are separated and the aqueous phase is extracted with dichloromethane (3×). The combined organic phases are dried over sodium sulphate and concentrated by evaporation. The title compound is identified on the basis of the Rf value from the residue by means of flash chromatography (SiO2 60 F).

29 4-Bromo-2-(4-methoxybutyl)pyridine

A solution of 3.17 mmol of 4-bromopyridine [1120-87-2] in 10 ml of tetrahydrofuran is cooled to −78° C. and a solution of 3.49 mmol of 4-methoxybutylmagnesium chloride [634590-61-7] in 5 ml of diethyl ether is added. 3.17 mmol of phenyl chloroformate are added dropwise and the reaction mixture is stirred at −78° C. for 10 minutes. Subsequently, the mixture is warmed to room temperature and quenched with 20% aqueous ammonium chloride solution. The phases of the filtrate are separated and the aqueous phase is extracted with diethyl ether. The combined organic phases are washed successively with water, 10% aqueous HCl, water and brine, dried over sodium sulphate and concentrated by evaporation. The residue is dissolved in 10 ml of toluene and 3.5 mmol of 3,4,5,6-tetrachloro-1,2-benzoquinone and 7 ml of acetic acid are added. The reaction mixture is stirred at room temperature for 24 hours and basified with 10% aqueous NaOH. The mixture is stirred at 0° C. for 15 minutes and filtered through Hyflo. The organic phase is extracted with 10% aqueous HCl (3×)—the combined aqueous phases are basified with 20% aqueous NaOH and extracted with dichloromethane (3×). The combined organic phases are dried over sodium sulphate and concentrated by evaporation. The title compound is identified on the basis of the Rf value from the residue by means of flash chromatography (SiO2 60 F).

Alternatively, 4-bromo-2-(4-methoxybutyl)pyridine can be prepared as follows:

a) A solution of 1.6 mmol of 4-bromo-2-(4-methoxybut-1 (E,Z)-enyl)pyridine in 30 ml of methanol is hydrogenated under a hydrogen atmosphere over 0.16 mmol of palladium/carbon at 0° C. for 40 minutes. The mixture is filtered off from the catalyst and concentrated by evaporation. The title compound is identified on the basis of the Rf value from the residue by means of flash chromatography (SiO2 60 F).

b) 4-Bromo-2-(4-methoxybut-1(E,Z)-enyl)pyridine

Analogously to residue 1a, 2.4 mmol of (3-methoxypropyl)triphenylphosphonium bromide [111088-69-8] and 1.6 mmol of 4-bromopyridine-2-carbaldehyde [131747-63-2] are reacted. The title compound (E,Z mixture) is identified on the basis of the Rf value.

31
4-Bromo-2-(3-methoxypropoxy)-6-methylpyridine

Analogously to residue 28, 21 mmol of 4-bromo-6-methyl-1H-pyridin-2-one are reacted. The title compound is identified on the basis of the Rf value.

The starting material is prepared as follows:

a) 4-Bromo-6-methyl-1H-pyridin-2-one 16 mmol of phosphorus oxybromide are added under an argon atmosphere to a solution of 21 mmol of 4-hydroxy-6-methyl-1H-pyridin-2-one [3749-51-7] in 9 ml of N,N-dimethyl-formamide. The reaction mixture is heated to 110° C. for 30 minutes—subsequently, the mixture is cooled to room temperature and 10 ml of water are added. The solution is brought to pH 7 by adding sodium carbonate and cooled to 0° C. The precipitate is filtered off and washed with water and diethyl ether. The title compound is identified on the basis of the Rf value.

32 4-Bromo-2-(4-methoxybutyl)-6-methyl pyridine

Analogously to residue 29, 3.17 mmol of 4-bromo-2-methylpyridine [22282-99-1] are reacted. The title compound is identified on the basis of the Rf value.

Alternatively, 4-bromo-2-(4-methoxybutyl)-6-methylpyridine can be prepared as follows:
a) Analogously to residue 29a, 1.6 mmol of 4-bromo-2-(4-methoxybut-1 (E,Z)-yl)-6-methylpyridine are reacted. The title compound is identified on the basis of the Rf value.

b) 4-Bromo-2-(4-methoxybut-1(E,Z)-yl)-6-methylpyridine

Analogously to residue 29b, 1.6 mmol of 4-bromo-6-methylpyridine-2-carbaldehyde [448906-71-6] are reacted. The title compound is identified on the basis of the Rf value.

33 4-Bromo-2-(4-methoxybutyl)-6-methylpyridine-N-oxide

According to methods known from the literature, the oxidation to residue 33 is carried out in the course of above described synthesis of residue 32. The title compound is identified on the basis of the Rf value.

34 6-Bromo-4-(3-methoxypropyl)-3,4-dihydro-2H-benzo[1,4]oxazine

The solution of 2.85 g of 6-bromo-4-(3-methoxypropyl)-4H-benzo[1,4]oxazin-3-one in 50 ml of tetrahydrofuran is admixed with 48 ml of 1M borane-tetrahydrofuran complex and stirred at 65° C. over 1 hour. The reaction mixture is cooled to room temperature and then admixed cautiously with 100 ml of methanol. After 10 minutes, the mixture is concentrated to dryness and the title compound is obtained as a yellowish oil from the residue by means of flash chromatography (SiO2 60 F). Rf=0.31 (1:2 EtOAc-heptane). Rt=4.89 (gradient I).

The starting material is prepared as follows:

a) 6-Bromo-4-(3-methoxypropyl)-4H-benzo[1,4]oxazin-3-one

The suspension of 9.87 g of 6-bromo-4H-benzo[1,4]oxazin-3-one [CAS 24036-52-0], 9.40 g of 1-chloro-3-methoxypropane, potassium fluoride on alumina (Fluka 60244), 0.144 g of potassium iodide in 500 ml of acetonitrile is stirred at 100° C. over 40 hours. The reaction mixture is cooled to room temperature and filtered through Hyflo, and the filtrate is concentrated by evaporation to dryness. The title compound is obtained as a slightly yellowish solid from the residue by crystallization from ethyl acetate. Rf=0.43 (1:1 EtOAc-heptane). Rt=4.27 (gradient I). m.p. 193-195° C.

35 6-Bromo-3-(3-methoxy-propyl)-imidazo[1,2-a]pyrimidine 20 mmol of 6-bromo-3-(3-methoxy-prop-1(E,Z)-yl)-imidazo[1,2-a]pyrimidine are reacted according to the procedure for residue 1. The title compound is identified on the basis of its Rf-value.

The starting materials are prepared in the following way:

a) 6-Bromo-3-(3-methoxy-prop-1(E,Z)-yl)-imidazo[1,2-a]pyrimidine 10 mmol of 6-bromo-imidazo[1,2-a]pyrimidine-3-carbaldehyde are reacted according to the procedure for residue 1a. The title compound is identified based its Rf-value.

b) 6-Bromo-imidazo[1,2-a]pyrimidine-3-carbaldehyde 10 mmol 6-bromo-imidazo[1,2-a]pyrimidine are reacted according to the procedure for residue 26b. The title compound is identified based on its Rf-value.

c) 6-Bromo-imidazo[1,2-a]pyrimidine 50 mmol of 5-bromo-pyrimidin-2-ylamine are dissolved in 200 ml of saturated aqueous sodium hydrogencarbonate solution. 55 mmol of chloroacetaldehyde are added to the reaction mixture and the mixture is stirred for 24 hours at 25° C. The mixture is extracted with ethyl acetate (3×300 ml) and the combined extracts are dried over sodium sulphate and evaporated under reduced pressure. Flash chromatography (SiO2 60 F) of the residue provides the title compound which is identified on the basis of its Rf-value.

36 5-Bromo-2-methoxy-3-(4-methoxy-butyl)-pyridine 0.16 mmol 10% Pd/C is added to a solution of 1.6 mmol 5-bromo-2-methoxy-3-(4-methoxybut-1(E,Z)-enyl)-pyridine in 30 ml methanol. The reaction mixture is stirred at 0° C. for 40 minutes under a hydrogen atmosphere. The catalyst is removed by filtration and. The title compound is obtained as a white solid from the residue by means of flash chromatography (SiO2 60 F).

The starting material is prepared as follows:

a) 5-Bromo-2-methoxy-3-(4-methoxy-but-1(E,Z)-enyl)-pyridine 2.45 ml of a 1M solution of sodium-bis(trimethylsilyl)amide in tetrahydrofuran are added to a suspension of 2.4 mmol (3-methoxy-propyl)-triphenyl-phosphonium bromide [111088-69-8] in 8 ml tetrahydrofuran under an argon atmosphere at 0° C. The reaction mixture is stirred for 30 minutes at 0° C. and then 1.6 mmol 5-bromo-2-methoxy-pyridine-3-carbaldehyde [103058-87-3] are added. The reaction mixture is warmed to room temperature and then diluted with tert-butyl methyl ether. The solution is washed with saturated aqueous sodium hydrogen-carbonate solution. The organic layer is dried over sodium sulphate, filtered and concentrated. The title compound is obtained from the residue by means of flash chromatography (SiO2 60 F) and identified based on its Rf value.

37 5-Bromo-2-methoxy-3-(3-methoxy-propoxy)pyridine

A mixture of 21 mmol 5-bromo-3-(3-methoxy-propoxy)-1H-pyridin-2-one, 14 mmol silver carbonate and 25 mmol iodomethane in 35 ml of benzene are stirred at 40-50° C. for 24 hours with exclusion of light. The mixture is cooled in an ice bath and the silver salts are removed by filtration. The filtrate is washed with 2% aqueous sodium hydrogencarbonate solution and with water (2×). The organic layer is dried over sodium sulphate, filtered and concentrated. The title compound is obtained from the residue by means of flash chromatography (SiO2 60 F) and identified based on its Rf value.

The starting material is prepared as follows:

a) 5-Bromo-3-(3-methoxy-propoxy)-1H-pyridin-2-one

To a 1.4M NaOH solution at 0° C. are added 0.9 mol 5-bromo-3-hydroxy-1H-pyridin-2-one [34206-49-0]. The mixture is allowed to stir for 15 minutes and 0.9 mmol 1-iodo-3-methoxypropane [61542-10-7] are added carefully at 0° C. The mixture is stirred at room temperature for 3 hours, then neutralized with acetic acid to pH 7. The mixture is extracted with chloroform (10×) and the organic layer is dried over sodium sulphate, filtered and concentrated. The title compound is obtained from the residue by means of flash chromatography (SiO2 60 F) and identified based on its Rf value.

38 2-Iodo-5-methoxy-4-(3-methoxy-propoxy)pyridine 2 mmol of 2,6-diiodo-3-methoxy-4-(3-methoxy-propoxy)-pyridine are added to a solution of 4 mmol n-butyllithium in 1.6 ml hexane and 10 ml tetrahydrofuran at −78° C. under an argon atmosphere. The reaction mixture is stirred at −78° C. for 15 minutes. 2 mmol of water are introduced and the reaction mixture is allowed to reach room temperature. 10% Aqueous ammonium chloride solution is added to the mixture followed by extraction with tert-butyl methyl ether (3×). The combined organic layers are dried over sodium sulphate, filtered and concentrated. The title compound is obtained from the residue by means of flash chromatography (SiO2 60 F) and identified based on its Rf value.

The starting material is prepared as follows:

a) 2,6-Diiodo-3-methoxy-4-(3-methoxy-propoxy)pyridine

To a stirred solution of 60 mmol NaOH in 50 ml N,N-dimethyl formamide is progressively added 50 mmol 2,6-diiodo-3-methoxy-pyridin-4-ol [437709-87-0]. The reaction mixture is stirred for 30 minutes and then cooled to 0° C. 60 mmol 1-iodo-3-methoxy-propane [61542-10-7] are added and the mixture is stirred for 15 minutes at room temperature. Water and ethyl acetate are added to the mixture, the layers are separated and the aqueous layer is extracted with ethyl acetate (3×). The combined organic layers are dried over sodium sulphate, filtered and concentrated. The title compound is obtained from the residue by means of flash chromatography (SiO2 60 F) and identified based on its Rf value,

39 2-Iodo-5-methoxy-4-(4-methoxy-butyl)-pyridine 2 mmol of 2,6-diiodo-3-methoxy-4-(4-methoxy-butyl)-pyridine are added to a solution of 4 mmol n-butyllithium in 1.6 ml hexane and 10 ml tetrahydrofuran at −78° C. under an argon atmosphere. The reaction mixture is stirred at −78° C. for 15 minutes. 2 mmol of water are introduced and the reaction mixture is warmed to room temperature. 10% Aqueous ammonium chloride solution is added to the mixture followed by extraction with tert-butyl methyl ether (3×). The combined organic layers are dried over sodium sulphate, filtered and concentrated. The title compound is obtained from the residue by means of flash chromatography (SiO2 60 F) and identified based on its Rf value.

The starting materials are prepared as follows:

a) 2,6-Diiodo-3-methoxy-4-(4-methoxy-butyl-pyridine

To a stirred solution of 60 mmol NaOH in 50 ml N,N-dimethyl formamide is progressively added 50 mmol 2,6-diiodo-4-(4-methoxy-butyl)-pyridin-3-ol. The reaction mixture is stirred for 30 minutes and then cooled to 0° C. 60 mmol methyl iodide are added and the mixture is stirred for 15 minutes at room temperature. Water and ethyl acetate are added to the mixture, the layers are separated and the aqueous layer is extracted with ethyl acetate (3×). The combined organic layers are dried over sodium sulphate, filtered and concentrated. The title compound is obtained from the residue by means of flash chromatography (SiO2 60 F) and identified based on its Rf value.

b) 2,6-Diiodo-4-(4-methoxy-butyl)-pyridin-3-ol

To a stirred solution of 0.1 mol 4-(4-methoxy-butyl)-pyridin-3-ol and 0.21 mol sodium carbonate in 1 l water at 20° C. is added 0.1 mol iodine. The mixture is stirred until the color disappears. The reaction mixture is adjusted to pH 3 with concentrated HCl. The formed solid is collected by filtration. The title compound is obtained from the solid by recrystallization from ethanol and identified based on its Rf value.

c) 4-(4-Methoxy-butyl)pyridin-3-ol

A mixture of 39 mmol acetic acid 4-(4-methoxy-butyl)-pyridin-3-yl ester in 20 ml acetic acid is heated to 70° C. for 30 minutes. After cooling, 75 ml of diethyl ether/pentane (1:5) is added and the precipitate is collected by filtration. The title compound is obtained from the solid by re-crystallization from toluene and identified based on its Rf value.

d) Acetic acid 4-(4-methoxy-butyl)-pyridin-3-yl ester

To a degassed solution of 9.9 mmol acetic acid 4-(4-methoxy-but-1-ynyl)-pyridin-3-yl ester and 0.51 mmol quinoline in 230 ml ethyl acetate is added 0.56 mmol 10% Pd/C. The suspension is vigorously stirred under an atmospheric pressure of hydrogen for 2 hours. The catalyst is removed by filtration and the solvent is evaporated. The title compound is obtained from the residue by means of flash chromatography (SiO2 60 F) and identified based on its Rf value.

e) Acetic acid 4-(4-methoxy-but-1-ynyl)pyridin-3-yl ester 0.95 mmol Palladium dichloride bis-triphenylphoshine and 0.97 mmol cupric chloride are dissolved in 64 ml tetrahydrofuran under an argon atmosphere. A solution of 30 mmol acetic acid 4-iodo-pyridin-3-yl ester [289473-46-7] and 38 mmol 4-methoxy-but-1-yne [36678-08-7] in 50 ml tetrahydrofuran is added in one portion and the reaction mixture is stirred at room temperature for 1 hour. 300 ml of diethyl ether are added and the precipitate is filtered off. The filtrate is washed successively with saturated, aqueous ammonium chloride solution (3×), water (2×) and brine. The organic layer is dried over sodium sulphate, filtered and concentrated. The title compound is obtained from the residue by means of flash chromatography (SiO2 60 F) and identified based on its Rf value.

40 6-Bromo-1-(3-methoxy-propyl)-3-methyl-1H-indazole

A mixture of 10.90 g methanesulfonic acid 2-acetyl-5-bromo-phenyl ester, 7.75 g of (3-methoxy-propyl)-hydrazine and 7.17 g of ammonium acetate in 100 ml of o-xylene is refluxed for 3 days with continuous separation of the water which is formed during the reaction. The reaction mixture is then cooled to room temperature and concentrated by evaporation. The title compound is obtained as an orange-yellow oil from the residue by means of flash chromatography (SiO2 60 F). Rf=0.38 (1:1 EtOAc-heptane). Rt=4.52 (gradient I).

The starting materials are prepared as follows:

a) Methanesulfonic acid 2-acetyl-5-bromo-phenyl ester 4.42 ml of methanesulphonyl chloride are added dropwise to a solution of 10.0 g 1-(4-bromo-2-hydroxy-phenyl)ethanone [30186-18-6] and 13.0 ml of triethylamine in 200 ml dichloromethane at 0° C. The reaction mixture is worked up after 1 hour by pouring into 250 ml cold 1N HCl and extracting with tert-butyl methyl ether (2×)—the combined organic layers are washed successively with water and brine, dried over sodium sulphate and concentrated by evaporation. The title compound is obtained as light yellow crystals from the residue by re-crystallization from diisopropyl ether. Rf=0.51 (1:1 EtOAc-heptane). Rt=3.94 (gradient I). m.p. 62.0-62.1° C.

b) (3-Methoxy-propyl)-hydrazine 22.0 g of 1-bromo-3-methoxy-propane [36865-41-5] are added dropwise to a mixture of 130 ml of hydrazine hydrate in 40 ml of ethanol at room temperature. After stirring for 2 hours, the reaction mixture is warmed to 40° C. for 1 hour, re-cooled to room temperature and then concentrated by evaporation. The residue is then continuously extracted with diethyl ether for 2 days—the cooled ether solution is dried over sodium sulphate and concentrated by evaporation to provide the crude title compound as a yellow oil, which is used in the next step without any further purification.

Residues NHR$^5$:

| *NHCH$_3$ | *NHCH$_2$CH$_3$ |
| A | B |
| *NHCH$_2$CH$_2$CH$_3$ | *NHCH(CH$_3$)$_2$ |
| C | D |
| *NHC(CH$_3$)$_3$ | *NHCH$_2$CH(CH$_3$)$_2$ |
| E | F |

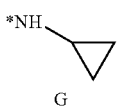
G

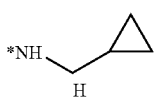
H

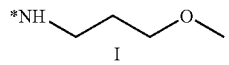
I

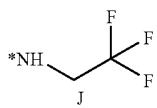
J

-continued
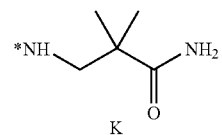
K
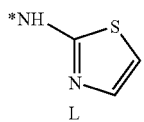
L
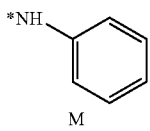
M
N
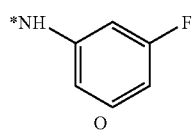
O
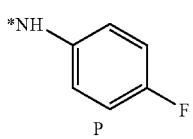
P
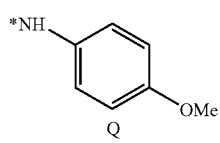
Q
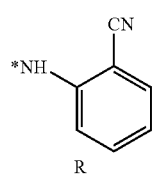
R
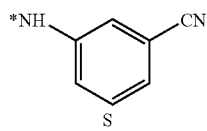
S
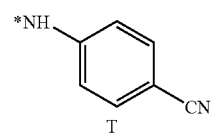
T
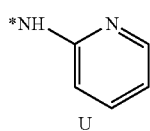
U
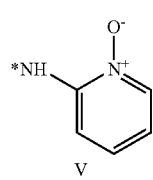
V
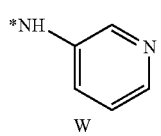
W
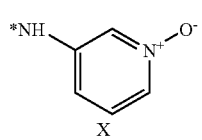
X
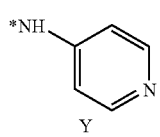
Y
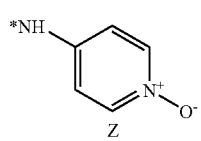
Z
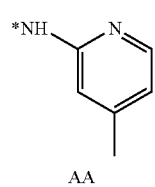
AA
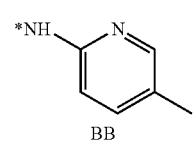
BB
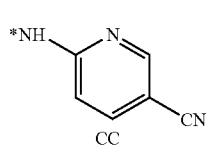
CC
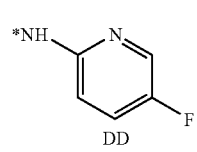
DD
-continued
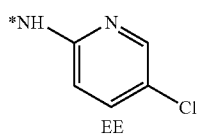
EE
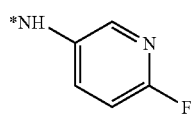
FF
GG
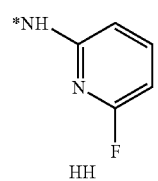
HH
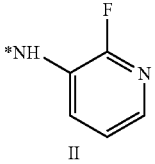
II
JJ
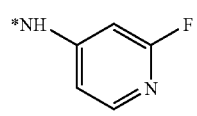
KK
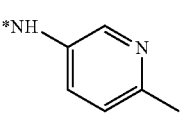
LL
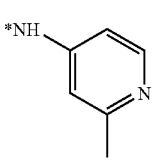
MM
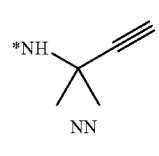
NN
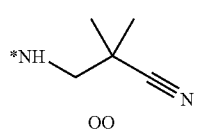
OO
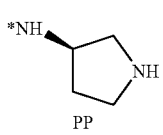
PP
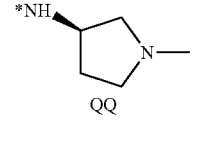
QQ
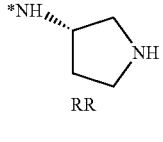
RR
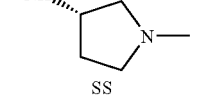
SS
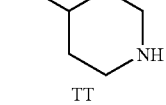
TT
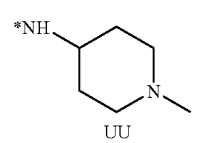
UU
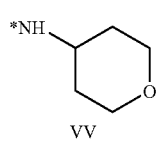
VV
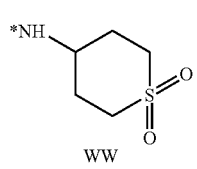
WW
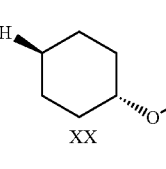
XX -continued

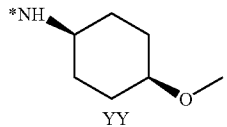

The protected or unprotected amines corresponding to above residues NR$^1$R$^2$ are commercially available and/or prepared according to methods known from the literature.

The Example Compounds 1A to 1YY correspond to the formula

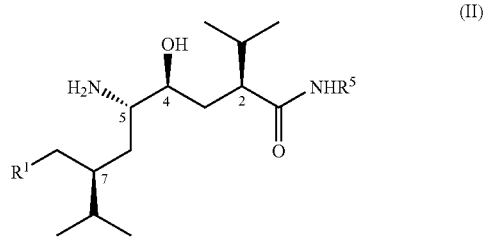

(II)

where R$^1$ corresponds to the above-specified residue 1 and NHR$^5$ in each Example Compound 1A to 1YY corresponds to one of the above-specified residues A to YY. The atoms denoted by * are the bonding sites. The further Example Compounds 2A to 40YY are accordingly the compounds of formula (II) in which the NHR$^5$ radical assumes all above residue-definitions (A to YY) for a given R$^1$ (above residue-definitions 2 to 40). Thus, example compound 1K is the compound N-(2-carbamoyl-2-methylpropyl)-5-amino-4-hydroxy-2-isopropyl-7-[3-(3-methoxypropyl)-1H-indol-5-ylmethyl]-8-methylnonanamide. Analogously to the preparation process described in detail herein below, the remaining compounds 1A to 40YY are obtained.

EXAMPLE 1K

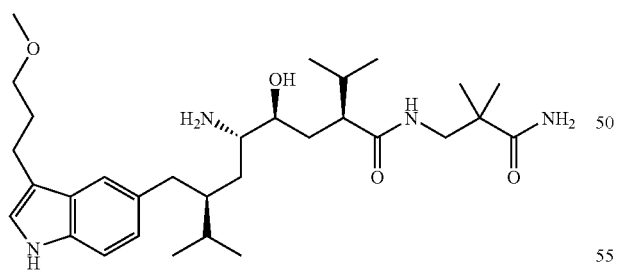

N-(2-Carbamoyl-2-methylpropyl)-5-amino-4-hydroxy-2-isopropyl-7-[3-(3-methoxypropyl)-1H-indol-5-ylmethyl]-8-methylnonanamide The solution of 0.048 g of N-(2-carbamoyl-2-methylpropyl)-5-amino-4-hydroxy-2-isopropyl-7-[3-(3-methoxypropyl)-1-(2-trimethylsilanylethoxymethyl)-1H-indol-5-ylmethyl]-8-methyl-nonanamide in 0.21 ml of tetrabutylammonium fluoride (1M in tetrahydrofuran) is concentrated by evaporation to dryness at room temperature under reduced pressure. The residue is admixed successively with 0.120 ml of N,N-dimethylformamide and 0.030 ml of ethylenediamine and stirred at 80° C. over 2 hours. The reaction mixture is cooled and extracted between water and tert-butyl methyl ether (2×). The organic phases are washed with brine, dried over sodium sulphate and filtered, and the filtrate is concentrated by evaporation. The title compound is obtained as a white foam from the residue by means of flash chromatography (SiO2 60 F). Rf=0.69 (40:10:1 dichloromethane-methanol-25% conc. ammonia). Rt=14.61 (gradient II).

The starting materials are prepared as follows:

a) N-(2-carbamoyl-2-methylpropyl)-5-amino-4-hydroxy-2-isopropyl-7-[3-(3-methoxypropyl)-1-(2-trimethylsilanylethoxymethyl)-1H-indol-5-ylmethyl]-8-methylnonanamide Analogously to method A, 0.356 g of benzyl (4-(2-carbamoyl-2-methylpropylcarbamoyl)-2-hydroxy-1-{2-[3-(3-methoxypropyl)-1-(2-trimethylsilanylethoxymethylyl)-1H-indol-5-ylmethyl]-3-methylbutyl}-5-methylhexyl)carbamate is used to obtain the title compound as a white foam. Rf=0.18 (200:20:1 dichloromethane-methanol-25% conc. ammonia). Rt=5.13 (gradient I).

b) Benzyl (4-(2-carbamoyl-2-methylpropylcarbamoyl)-2-hydroxy-1-{2-[3-(3-methoxypropyl)-1-(2-trimethylsilanylethoxymethyl)-1H-indol-5-ylmethyl]-3-methylbutyl}-5-methylhexyl)carbamate The mixture of 0.420 g of benzyl {1-(4-isopropyl-5-oxotetrahydrofuran-2-yl)-3-[3-(3-methoxypropyl)-1-(2-trimethylsilanylethoxymethyl)-1H-indol-5-ylmethyl]-4-methylpentyl}carbonate, 0.208 g of 3-amino-2,2-dimethylpropionamide, 0.059 g of 2-hydroxypyridine and 0.414 ml of triethylamine is stirred at 70° C. over 22 hours. The reaction mixture is cooled, admixed with 1M sodium hydrogencarbonate solution and extracted with tert-butyl methyl ether (2×). The combined organic phases are washed with water and brine, dried over sodium sulphate and filtered, and the filtrate is concentrated by evaporation. The title compound is obtained as a white foam from the residue by means of flash chromatography (SiO2 60 F). Rf=0.17 (95:5 dichloromethane-methanol). Rt=5.79 (gradient I).

c) Benzyl {1-(4-isopropyl-5-oxotetrahydrofuran-2-yl)-3-[3-(3-methoxypropyl)-1-(2-trimethylsilanylethoxymethyl)-1H-indol-5-ylmethyl]-4-methylpentyl}carbonate The stirred solution of 1.52 g of 5-{1-amino-3-[3-(3-methoxypropyl)-1-(2-trimethylsilanylethoxymethyl)-1H-indol-5-ylmethyl]-4-methylpentyl}-3-isopropyldihydrofuran-2-one in 25 ml of ethyl acetate is admixed at 0° C. successively with 25 ml of saturated sodium carbonate solution and 0.514 ml of benzyl chloroformate. The reaction mixture is stirred at 0° C. over 1 hour. The resulting mixture is admixed with water and extracted with tert-butyl methyl ether (2×). The organic phases are washed successively with 1M sodium hydrogencarbonate solution and brine, dried over sodium sulphate and filtered, and the filtrate is concentrated by evaporation. The title compound is obtained as slightly yellowish crystals from the residue by means of flash chromatography (SiO2 60 F). Rf=0.39 (1:2 EtOAc-heptane). Rt=29.7 (gradient II). m.p. 99-101° C.

d) 5-{1-Amino-3-(3-[3-methoxypropyl)-1-(2-trimethylsilanylethoxymethyl)-1H-indol-5-yl-methyl]-4-methylpentyl}-3-isopropyldihydrofuran-2-one The stirred solution of 1.86 g of 2-[2 azido-2-(4-isopropyl-5-oxotetrahydrofuran-2-yl)ethyl]-1-[3-(3-methoxypropyl)-1-(2-trimethylsilanylethoxymethyl)-1H-indol-5-yl]-3-methylbutyl methoxyacetate (diastereomer mixture) in 100 ml of ethanol is hydrogenated at 0° C. in the presence of 0.165 ml of ethanolamine and 1.88 g of 10% Pd/C over 6 hours. The reaction mixture is clarified by filtration and the filtrate is concentrated by evaporation. The residue is admixed with 100 ml of 1M sodium hydrogencarbonate solution and extracted with tert-butyl methyl ether (3×). The combined organic phases are dried over sodium sulphate and filtered, and the filtrate is concentrated by evaporation. The crude title compound is obtained as a colourless oil from the residue by means of flash chromatography (SiO2 60 F). Rt=24.2 (gradient II).

e) 2-[2-Azido-2-(4-isopropyl-5-oxotetrahydrofuran-2-yl)ethyl]-1-[3-(3-methoxypropyl)-1-(2-trimethylsilanylethoxymethyl)-1H-indol-5-yl]-3-methylbutyl methoxyacetate (diastereomer mixture)

The stirred solution of 0.155 g of 5-(1-azido-3-{(R,S)-hydroxy-[3-(3-methoxypropyl)-1-(2-trimethylsilanylethoxymethyl)-1H-indol-5-yl]methyl}-4-methylpentyl)-3-isopropyldihydrofuran-2-one (diastereomer mixture) in 3.0 ml of toluene is admixed at 0° C. successively with 0.049 ml of pyridine, 0.052 ml of methoxyacetyl chloride and 0.003 g of 4-dimethylaminopyridine. The reaction mixture is stirred at room temperature over 16 hours. The resulting mixture is admixed with water and extracted with tert-butyl methyl ether (2×). The combined organic phases are washed successively with 1M sodium hydrogencarbonate solution, water and brine, dried over sodium sulphate and filtered, and the filtrate is concentrated by evaporation. The title compound (diastereomer mixture) is obtained as a slightly yellowish oil from the residue by means of flash chromatography (SiO2 60 F). Rf=0.28/0.24 (1:2 EtOAc-heptane). Rt=28.2/28.6 (gradient II).

f) 5-(1-Azido-{(R,S)-hydroxy-[3-(3-methoxypropyl)-1-(2-trimethylsilanylethoxymethyl)-1H-indol-5-yl]methyl}-4-methylpentyl)-3-isopropyldihydrofuran-2-one (diastereomer mixture)

The stirred solution of 0.50 ml of dibutyl magnesium (1M in heptane) in 2.0 ml of tetrahydrofuran is cooled to 0° C. and admixed with 0.31 ml of n-butylithium (1M in hexane). After 10 minutes, the mixture is admixed with the solution of 0.204 g of 5-bromo-3-(3-methoxypropyl)-1-(2-trimethylsilanylethoxymethyl)-1H-indole (residue 1) in 0.5 ml of tetrahydrofuran and stirred at 0° C. for a further 30 minutes. The reaction mixture is cooled to −78° C. and admixed over 2 minutes with the solution of 0.142 g of 2-[2 azido-2-(4-isopropyl-5-oxotetrahydrofuran-2-yl)ethyl]methylbutyldehyde [173154-02-4] in 0.5 ml of tetrahydrofuran. The resulting mixture is stirred at −78° C. for a further 30 minutes and subsequently successively quenched with 1M ammonium chloride solution, diluted with water and extracted with tert-butyl methyl ether (2×). The combined organic phases are washed with brine, dried over sodium sulphate and filtered, and the filtrate is concentrated by evaporation. The title compound (diastereomer mixture) is obtained as a slightly yellowish oil from the residue by means of flash chromatography (SiO2 60 F). Rf=0.25 (1:2 EtOAc-heptane). Rt=26.9/28.1 (gradient II).

EXAMPLE 3DD

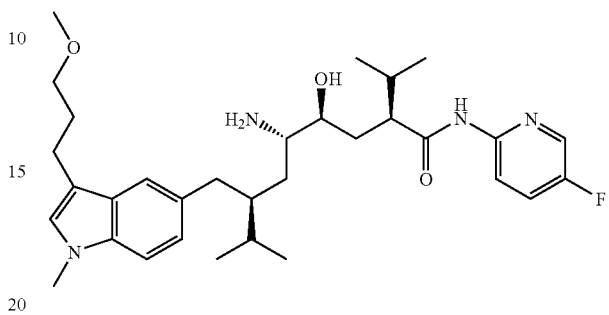

5-Amino-4-hydroxy-2-isopropyl-7-[3-(3-methoxypropyl)-1-methyl-1H-indol-5-ylmethyl]-8-methyl-nonanoic acid (5-fluoro-pyridin-2-yl)-amide To the solution of 0.090 g (4-(5-fluoro-pyridin-2-ylcarbamoyl)-2-hydroxy-1-{2-[3-(3-methoxypropyl)-1-methyl-1H-indol-5-ylmethyl]-3-methyl-butyl}-5-methyl-hexyl)carbamic acid tert-butyl ester in 2.4 ml dichloromethane are added 1.2 ml trifluoroacetic acid at 0° C. The reaction mixture is stirred at 0° C. for 1 hour and then concentrated by evaporation. The title compound is obtained as a beige foam from the residue by means of flash chromatography (SiO2 60 F). Rf=0.35 (200:20:1 dichloromethane-methanol-25% conc. ammonia). Rt=4.58 (gradient I).

The starting materials are prepared as follows:

a) (4-(5-Fluoro-pyridin-2-ylcarbamoyl)-2-hydroxy-1-{2-[3-(3-methoxy-propyl)-1-methyl-1H-indol-5-ylmethyl]-3-methyl-butyl}-5-methyl-hexyl)-carbamic acid tert-butyl ester To the solution of 0.210 g 5-tert-butoxycarbonylamino-4-(tert-butyl-dimethyl-silanyloxy)-2-isopropyl-7-[3-(3-methoxy-propyl)-1-methyl-1H-indol-5-ylmethyl]-8-methyl-nonanoic acid in 3.0 ml dichloromethane are added 0.076 ml 1-chloro-N,N-2-trimethylpropenyamine at 0° C. The reaction mixture is stirred at 0° C. for 1 hour and then concentrated by evaporation. The residue is re-dissolved in 2.0 ml dichloromethane and added to the solution of 0.042 g 2-amino-5-fluoropyridine, 0.046 ml triethylamine in 2.0 ml dichloromethane at 0° C. The mixture is stirred at room temperature for 16 hours. The reaction mixture is extracted between water and tert-butyl methyl ether (2×). The combined organic layers are washed with brine, dried over sodium sulphate, filtered, and the filtrate concentrated by evaporation. The residue is dissolved in 3.0 ml tetrahydrofuran and 0.445 ml of tetrabutylammonium fluoride (1M tetrahydrofuran) are added at 0° C. The reaction mixture is stirred for 1 hour and then extracted between 1M sodium hydrogencarbonate solution and tert.-butyl methyl ether (2×). The combined organic layers are washed with brine, dried over sodium sulphate, filtered, and the filtrate concentrated by evaporation. The title compound is obtained as a beige oil from the residue by means of flash chromatography (SiO2 60 F). Rf=025 (1:1 EtOAc-heptane). Rt=5.68 (gradient I).

b) 5-tert-Butoxycarbonylamino-4-(tert-butyl-dimethyl-silanyloxy)-2-isopropyl-7-[3-(3-methoxy-propyl)-1-methyl-1H-indol-5-ylmethyl]-8-methyl-nonanoic acid To the mixture of 0.235 g {1-(4-Isopropyl-5-oxo-tetrahydro-furan-2-yl)-3-[3-(3-methoxypropyl)-1-methyl-1H-indol-5-ylmethyl]-4-methyl-pentyl}-carbamic acid tert-butyl ester in 2 ml dioxan and 2 ml water are added 0.018 g lithium hydroxide monohydrate. After stirring at room temperature for 24 hours, the resulting solution is concentrated by evaporation at 25° C. and the residue is extracted between water-ice, 1M citric acid and tert.-butyl methyl ether (2×). The combined organic phases are washed with water, brine and concentrated by evaporation at 25° C. The residue is immediately dissolved in DMF, treated with 0.255 g imidazole and 0.321 g tert.-butyldimethylchlorosilane and stirred for 24 hours at room temperature. The resulting mixture is concentrated by evaporation. The residue is dissolved in water, the pH is adjusted to 4.0 with 1M citric acid followed by extraction with diethyl ether (2×). The combined organic phases are concentrated by evaporation and the residue is dissolved in 1.5 ml tetrahydrofuran, 1.5 ml water and 3.8 ml acetic acid. The mixture is stirred at room temperature for 2 hours, extracted between water-ice and diethyl ether (2×). The combined organic layers are washed with water and brine, dried over sodium sulphate, filtered, and the filtrate concentrated by evaporation. The title compound is obtained as a white foam from the residue by means of flash chromatography (SiO2 60 F). Rf=0.32 (1:1 EtOAc-heptane). Rt=6.96 (gradient I).

c) {1-(4-Isopropyl-5-oxo-tetrahydro-furan-2-yl)-3-[3-(3-methoxy-propyl)-1-methyl-1H-indol-5-ylmethyl]-4-methyl-pentyl}-carbamic acid tert-butyl ester To the solution of 0.220 g 5-{1-amino-3-[3-(3-methoxypropyl)-1-methyl-1H-indol-5-ylmethyl]-4-methyl-pentyl}-3-isopropyl-dihydro-furan-2-one in 10 ml dichloromethane are added 0.105 ml N,N-diisopropylethylamine and 0.134 g di-tert-butyl dicarbonate at 0° C. The mixture is stirred at room temperature for 16 hours and then concentrated by evaporation. The title compound is obtained as a white foam from the residue by means of flash chromatography (SiO2 60 F). Rf=0.29 (1:2 EtOAc-heptane). Rt=5.94 (gradient I).

d) 5-{1-Amino-3-[3-(3-methoxy-propyl)-1-methyl-1H-indol-5-ylmethyl]methyl-pentyl}-3-isopropyl-dihydro-furan-2-one Analogously to Example 1K (steps d-f), 5-bromo-(3-methoxypropyl)-1-methyl-1H-indole (residue 3) and 2-[2-azido-2-(4-isopropyl-5-oxotetrahydrofuran-2-yl)ethyl]-3-methyl-butyraldehyde [173154-02-4] are used to obtain the title compound as a colourless oil. Rf=0.57 (200:20:1 dichloromethane-methanol-25% conc. ammonia). Rt=4.43 (gradient I).

The invention claimed is:
1. Compound of the general formula

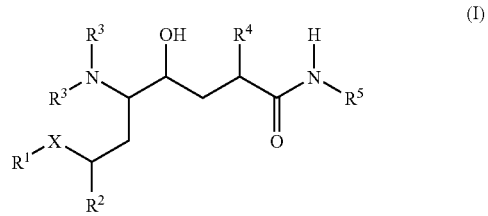

where

X is —$CH_2$—;

$R^1$ is a radical selected from the group consisting of benzoimidazolyl, di-$C_{1-6}$-alkoxypyrimidinyl, 2- or 5-benzo[b]thienyl, 6- or 7-isoquinolyl, 6- or 7-tetrahydroquinolyl, 6- or 7-tetrahydroisoquinolyl, 6-quinoxalinyl, 6- or 7-quinazolinyl, dihydro-3H-benzo[1,4]oxazinyl, 3,4-dihydro-2H-benzo[1,4]oxazinyl, 3-oxo-4H-benzo[1,4]oxazinyl, 2-oxobenzooxazolyl, 2-oxo-1,3-dihydroindolyl, 2,3-dihydroindolyl, indazolyl, benzofuranyl, 6- or 7-quinolyl, 6- or 7-isoquinolyl, 6- or 7-tetrahydroquinolyl, oxotetrahydroquinolyl, 6- or 7-tetrahydroisoquinolyl, 6-quinoxalinyl, 6- or 7-quinazolinyl, indolyl, 3-oxo-3,4-dihydro-2H-benzo[1,4]oxazinyl, 2-oxo-2,3-dihydrobenzooxazolyl, 2,3-dihydrobenzothiazinyl, imidazolyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl, [1,2,4]triazolo[4,3-a]pyridinyl, imidazo[1,5-a]pyridinyl and imidazo[1,2-a]pyrimidinyl, each of which is substituted by from one to four radicals selected from hydroxy, halogen, oxo, oxide, carbamoyl, carboxyl, cyano, trifluoromethyl, $C_{1-6}$-alkyl, $C_{1-6}$-alkoxy, hydroxy-$C_{1-6}$-alkoxy, $C_{1-6}$-alkoxy-$C_{1-6}$-alkyl, $C_{1-6}$-alkoxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkoxy, pyridylcarbamoyloxy-$C_{1-6}$-alkoxy, 3-morpholino-2-hydroxypropoxy, benzyloxy-$C_{1-6}$-alkoxy, picolyloxy, $C_{1-6}$-alkoxycarbonyl, $C_{1-6}$-alkoxy-$C_{1-6}$-alkoxy-$C_{1-6}$-alkyl, $C_{1-6}$-alkylcarbonylamino, $C_{1-6}$-alkylcarbonylamino-$C_{1-6}$-alkyl, $C_{1-6}$-alkylcarbonylamino-$C_{1-6}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$-alkylcarbonylamino-$C_{1-6}$-alkoxy, $C_{3-6}$-cycloalkylcarbonylamino-$C_{1-6}$-alkyl, $C_{3-6}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{1-6}$-alkoxy-$C_{1-6}$-alkyl, hydroxy-$C_{1-6}$-alkoxy-$C_{1-6}$-alkoxy, $C_{1-6}$-alkoxycarbonylamino-$C_{1-6}$-alkyl, $C_{1-6}$-alkoxycarbonylamino-$C_{1-6}$-alkoxy, $C_{1-6}$-alkylaminocarbonylamino-$C_{1-6}$-alkyl, $C_{1-6}$-alkylaminocarbonylamino-$C_{1-6}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxo-oxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$- alkoxycarbonyl-$C_{1-6}$-alkoxy, $C_{1-6}$-alkylsulphonylamino-$C_{1-6}$-alkyl, $C_{1-6}$-alkylsulphonylamino-$C_{1-6}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, $C_{1-6}$-alkylamino-$C_{1-6}$-alkyl, $C_{1-6}$-alkylamino-$C_{1-6}$-alkoxy, di-$C_{1-6}$-alkylamino-$C_{1-6}$-alkyl, di-$C_{1-6}$-alkylamino-$C_{1-6}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkyl-carbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxy-aminocarbonyl-$C_{1-6}$-alkyl, 6-alkoxyaminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylamino-carbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkl, piperazinoalkyl, piperazinoalkoxy, piperazinoalkoxyalkyl, [1,2,4]triazol-1-ylalkyl, [1,2,4]triazol-1-ylalkoxy, [1,2,4]triazol-4-ylalkyl, [1,2,4]triazol-4-ylalkoxy, [1,2,4]oxadiazol-5-ylalkyl, [1,2,4]oxadiazol-5-ylalkoxy, 3-methyl[1,2,4]oxadiazol-5-ylalkyl, 3-methyl[1,2,4]oxadiazol-5-ylalkoxy, 5-methyl[1,2,4]oxadiazol-3-ylalkyl, 5-methyl[1,2,4]oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-yl-alkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl and 2-oxotetrahydropyrimidinyl;

$R^2$ is $C_1$-$C_6$-alkyl;

$R^3$ is H;

$R^4$ is $C_1$-$C_6$-alkyl;

$R^5$ is $C_1$-$C_6$-alkyl, halo-$C_1$-$C_6$-alkyl, $C_1$-$C_6$-alkoxy-$C_1$-$C_6$-alkyl, $C_2$-$C_8$-alkynyl, cyano-$C_1$-$C_6$-alkyl, optionally substituted $C_3$-$C_6$-cycloalkyl, $C_3$-$C_8$-cycloalkyl-$C_1$-$C_6$-alkyl, optionally substituted aryl, optionally substituted heterocyclyl-$C_0$-$C_6$-alkyl which, for $C_0$-alkyl, is bonded via a carbon atom or $H_2N$—$C(O)$—$C_1$-$C_6$-alkyl;

or in which one or more atoms have been replaced by their stable non-radioactive isotopes, or a pharmaceutically acceptable salt thereof.

2. A pharmaceutical preparation comprising, as an active pharmaceutical ingredient, a compound according to claim 1 in free form or as a pharmaceutically acceptable salt, and a pharmaceutically inert excipient.

* * * * *